US005683912A

United States Patent [19]

Elgoyhen et al.

[11] Patent Number: 5,683,912

[45] Date of Patent: Nov. 4, 1997

[54] CLONING AND EXPRESSION OF A NOVEL ACETYLCHOLINE-GATED ION CHANNEL RECEPTOR SUBUNIT

[75] Inventors: Ana Belen Elgoyhen, Del Mar; David S. Johnson, La Jolla; James Richard Boulter, San Diego; Stephen Fox Heinemann, La Jolla, all of Calif.

[73] Assignee: The Salk Institute for Biological Studies, La Jolla, Calif.

[21] Appl. No.: 278,635

[22] Filed: Jul. 21, 1994

[51] Int. Cl.$^6$ .............................. C12N 5/10; C12N 15/12

[52] U.S. Cl. .................. 435/252.3; 435/69.1; 435/320.1; 536/23.5

[58] Field of Search ................................ 435/69.1, 252.3, 435/320.1; 530/350; 536/23.5

[56] References Cited

PUBLICATIONS

Boulter et al., *Nature* 319:368–374, 30 Jan. 1986.

Mulle et al., "Calcium Influx through Nicotinic Receptor in Rat Central Neurons: Its Relevance to Cellular Regulation" *Neuron* 8:135–143 (1992).

Noda et al., "Cloning and sequence analysis of calf cDNA and human genomic DNA encoding α–subunit precursor of muscle acetylcholine receptor" *Nature* 305(27):818–823 (1983).

Seguela et al., "Molecular Cloning, Functional Properties, and Distribution of Rat Brain $\alpha_7$: A Nicotinic Cation Channel Highly Permeable to Calcium" *The Journal of Neuroscience* 13(2):596–604 (1993).

Shirley, S.G., "Olfaction" *International Review of Neurobiology* 33:1–53 (1992).

Sine and Steinbach, "Agonists Block Currents Through Acetylcholine Receptor Channels" *Biophys. J.* 46:277–284 (1984).

Taylor, Palmer,, "Agents Acting at the Neuromuscular Junction and Autonomic Ganglia" *Goodman and Gilman's The Pharmacological Basis of Therapeutics* Chapter 9:166–186 (1990).

Taylor, Palmer,, "Cholinergic Agonists" *Goodman and Gilman's The Pharmacological Basis of Therapeutics* Chapter 6:122–149 (1990).

Vernallis et al., "Neurons Assemble Acetylcholine Receptor with as Many as Three Kinds of Subunits While Maintaining Subunit Segregation Among Receptor Subtypes" *Neuron* 110:451–464 (1993).

Von Heijne, Gunnar, "A new method for predicting signal sequence cleavage sites" *Nucleic Acids Research* 14(11):4683–4691 (1986).

Wittkowski et al., "The pars tuberalis of the hypophysis: a modulator of the pars distalis"? *Acta Endocrinologica* 126:285–290 (1992).

Ballivet et al., "Electrophysiology of a Chick Neuronal Nicotinic Acetylcholine Receptor Expressed in Xenopus Oocytes after cDNA Injection" *Neuron* 1:847–852 (1988).

Boulter et al., "α3, α5, and β4: Three Members of the Rat Neuronal Nicotinic Acetylcholine Receptor–related Gene Family Form a Gene Cluster" *The Journal of Biological Chemistry* 265(8):4472–4482 (1990).

Brown and Nuttall, "Efferent Control Of Cochlear Inner Hair Cell Responses In The Guinea–Pig" *Journal of Physiology* 354:625–646 (1984).

Buonanno et al., "Isolation and Characterization of the β and ε Subunit Genes of Mouse Muscle Acetylcholine Receptor" *The Journal of Biological Chemistry* 264(13):7611–7616 (1989).

Chomczynski and Sacchi, "Single–Step Method of RNA Isolation by Acid Guanidinium Thiocyanate–Phenol–Chloroform Extraction" *Analytical Biochemistry* 162:156–159 (1987).

Couturier et al., "α5, α3, and Non–α3, Three Clustered Avian Genes Encoding Neuronal Nicotinic Acetylcholine Receptor–Related Subunits" *The Journal Of Biological Chemistry* 265(29):17560–17567 (1990).

Dennis et al., "Amino Acids of the *Torpedo marmorata* Acetylcholine Receptor α Subunit Labeled by a Photoaffinity Ligand for the Acetylcholine Binding Site" *Biochemistry* 27:2346–2357 (1988).

Fuchs and Murrow, "Cholinergic Inhibition of Short (Outer) Hair Cells of the Chick's Cochlea" *The Journal of Neuroscience* 12(3):800–809 (1992).

(List continued on next page.)

*Primary Examiner*—John Ulm

*Attorney, Agent, or Firm*—Gray Cary Ware & Freidenrich; Stephen E. Reiter

[57] ABSTRACT

The present invention provides isolated nucleic acids encoding alpha9 nicotinic acetylcholine receptor subunit and receptor subunit protein encoded thereby. Also provided are vectors containing the invention nucleic acids, host cells transformed therewith, alpha9 nicotinic acetylcholine receptor subunit and functional nicotinic acetylcholine receptors comprising at least one alpha9 subunit expressed recombinantly in such host cells as well as transgenic non-human mammals that express the invention receptor subunit and mutants thereof. Receptors of the invention comprise at least one alpha9 nicotinic acetylcholine subunit and form cationic channels activated by acetylcholine, but blocked by nicotine and muscarine. The invention also provides methods for identifying compounds that modulate the ion channel activity of the functional invention receptors containing at least one invention subunit.

13 Claims, 13 Drawing Sheets

PUBLICATIONS

Fuxe et al., "Neuroendocrine Actions of Nicotine And Of Exposure To Cigarette Smoke: Medical Implications" *Psychoneuroendocrinology* 14(1&2):19–41 (1989).

Galzi et al., "Functional Architecture Of The Nicotinic Acetylcholine Receptor: From Electric Organ to Brain" *Annual Review of Pharmacology* 31:37–72 (1991).

Galzi et al., "Identification of a Novel Amino Acid α–Tyrosine 93 within the Cholinergic Ligands–bindng Sites of the Acetylcholine Receptor by Photoaffinity Labeling" *The Journal of Biological Chemistry* 265(18):10430–10437 (1990).

Kakehati et al., "Cellular Mechanism of Acetylcholine–Induced Response In Dissociated Outer Hair Cells Of Guinea–Pig Cochlea" *Journal of Physiology* 463:227–244 (1993).

Klinke, Rainer, "Neurotransmission in the inner ear" *Hearing Research* 22:235–243 (1986).

Kyte and Doolittle, "A Simple Method for Displaying the Hydropathic Character of a Protein" *Molecular Biology* 157:105–132 (1982).

Liman et al., "Subunit Stoichiometry of a Mammalian $K^+$Channel Determined by Consruction of Multimeric cDNA's" *Neuron* 9:861–871 (1992).

Miledi and Parker, "Chloride Current Induced By Injection of Calcium Into *Xenopus Oocytes*" *Journal of Physiology* 357:173–183 (1984).

Mishina et al., "Molecular distinction between fetal and adult forms of muscle acetylcholine receptor" *Nature* 321(22):406–411 (1986).

```
 -153

 -120  ACA GAA GTG GGA GTC CTC GCT GTC TGC CTG ACA CAT TCT
  -22


    1  GTA GAG ACA GCA AAT GGG AAA TAT GCT CAG AAA TTG TTC
    1  Val Glu Thr Ala Asn Gly Lys Tyr Ala Gln Lys Leu Phe
                                      ↓
  121  ACG CTC TCC CAG ATA AAG GAC ATG GAC GAG AGA AAC CAG
   41  Thr Leu Ser Gln Ile Lys Asp Met Asp Glu Arg Asn Gln

  241  GAC TCC ATC AGG ATT CCC AGC GAT CTG GTG TGG AGG CCG
   81  Asp Ser Ile Arg Ile Pro Ser Asp Leu Val Trp Arg Pro

  361  ATC ACC TGG GAC TCA CCG GCC ATC ACC AAA AGC TCC TGT
  121  Ile Thr Trp Asp Ser Pro Ala Ile Thr Lys Ser Ser Cys

  481  GTG GAC ATA TTC AAT GCC CTG GAC AGC GGT GAC CTC TCT
  161  Val Asp Ile Phe Asn Ala Leu Asp Ser Gly Asp Leu Ser

  601  CCT TAC CCA GAT GTC ACC TTC ACT CTC CTT CTG AAG AGG
  201  Pro Tyr Pro Asp Val Thr Phe Thr Leu Leu Leu Lys Arg


  721  GCA GCC TCT GGG GAG AAG GTC TCT CTG GGA GTG ACC ATC
  241  Ala Ala Ser Gly Glu Lys Val Ser Leu Gly Val Thr Ile
                                   -----------------------
       -------

  841  TAC ATA GCT ACC ATG GCC TTG ATC ACT GCC TCC ACA GCC
  281  Tyr Ile Ala Thr Met Ala Leu Ile Thr Ala Ser Thr Ala
       ---------------------------MSR III----------------

  961  AAG TAC ATG TCC AGG ATC TTG TTT GTC TAC GAT GTG GGT
  321  Lys Tyr Met Ser Arg Ile Leu Phe Val Tyr Asp Val Gly

 1081  AAA ACG TCC AGA AAC AAA GAC CTT TCC AGA AAG AAG GAA
  361  Lys Thr Ser Arg Asn Lys Asp Leu Ser Arg Lys Lys Glu

 1201  GCA CTG GCG AAA AAT ATC GAA TAC ATT GCC AAG TGC CTC
  401  Ala Leu Ala Lys Asn Ile Glu Tyr Ile Ala Lys Cys Leu


 1321  TTC TTT GCT ATG GTG TTT GTC ATG ACC GTC TTG ATC ATA
  441  Phe Phe Ala Met Val Phe Val Met Thr Val Leu Ile Ile
       --MSR IV-------------------------------------------

 1441  TCT GCC CCA GCG TGT GAG TTC AGC TGC TGT TCA TAC ATA
 1561  GAT GCA AGG TTT CAA GGG TAA AGG GCT GGA GGA AGA GAG
 1681  CAA CAA AGC ACA GTG TAT TCC TGC TTA AGA TTT AAA GCA
```

FIG. 1A

```
ACA TGT TGG GAA AAG ATG AAC CGG CCC CAT TCC TGC CTC TCC
                    Met Asn Arg Pro His Ser Cys Leu Ser
                    -----------------------------------

AGC GAT CTT TTT GAA GAC TAC TCC AGT GCT CTG CGT CCA GTC
Ser Asp Leu Phe Glu Asp Tyr Ser Ser Ala Leu Arg Pro Val

ATT CTG ACA GCC TAT CTA TGG ATC CGC CAA ACC TGG CAC GAT
Ile Leu Thr Ala Tyr Leu Trp Ile Arg Gln Thr Trp His Asp
                         ↓
GAC ATT GTC CTA TAC AAC AAG GCT GAC GAT GAG TCT TCA GAG
Asp Ile Val Leu Tyr Asn Lys Ala Asp Asp Glu Ser Ser Glu

GTG GTG GAT GTC ACC TAC TTC CCT TTT GAC AGC CAG CAG TGC
Val Val Asp Val Thr Tyr Phe Pro Phe Asp Ser Gln Gln Cys

GAC TTC ATT GAA GAT GTG GAA TGG GAG GTC CAT GGC ATG CCT
Asp Phe Ile Glu Asp Val Glu Trp Glu Val His Gly Met Pro

AGG TCC TCC TTC TAC ATC GTC AAC CTC CTC ATC CCT TGC GTC
Arg Ser Ser Phe Tyr Ile Val Asn Leu Leu Ile Pro Cys Val
    ---------------------------------------------------

CTA TTG GCC ATG ACT GTG TTT CAG CTA ATG GTG GCA GAG ATC
Leu Leu Ala Met Thr Val Phe Gln Leu Met Val Ala Glu Ile
-----------------MSR II--------------------------------

CTT ACC ATC ATG GTG ATG AAT ATT CAC TTC TGT GGA GCT GAG
Leu Thr Ile Met Val Met Asn Ile His Phe Cys Gly Ala Glu
---------------------------

GAG AGC TGC CTT AGT CCC CGC CAC AGC CAG GAG CCA GAA CAA
Glu Ser Cys Leu Ser Pro Arg His Ser Gln Glu Pro Glu Gln

GTA AGA AAA CTC TTA AAG AAT GAC CTG GGG TAC CAG GGT GGG
Val Arg Lys Leu Leu Lys Asn Asp Leu Gly Tyr Gln Gly Gly

AAG GAC CAC AAG GCC ACC AAC TCC AAG GGC AGC GAG TGG AAG
Lys Asp His Lys Ala Thr Asn Ser Lys Gly Ser Glu Trp Lys

GCA AGA GCA GAT TAG CAG GAA AGA GGA GTG GGC TGG TAG GCA
Ala Arg Ala Asp
---------------

ATT TAG GGG ATA GGT TGC GTA TGC TTT TAT TCC TAA CTT CAA
TTA GAA AGG ACC CTT TCA CAG GCT CCC ATG AAG GGG AGT GGT
AGA AAA GAC AAA ACA AAT TCA TTC TCT TAG TCC TTA ATA AAA
```

FIG. 1B

```
        GGT GGC AGT GAG GGT GTT TTG AGC CCT TCA CAG  -121
                                                ↓
    TTT TGC TGG ATG TAT TTT GCT GCT TCT GGA ATC AGA GCC   -1
    Phe Cys Trp Met Tyr Phe Ala Ala Ser Gly Ile Arg Ala   -1
   -SIGNAL PEPTIDE--------------------------------------

    GAG GAT ACG GAC GCG GTG CTG AAT GTT ACA CTG CAG GTC  120
    Glu Asp Thr Asp Ala Val Leu Asn Val Thr Leu Gln Val   40

    GCG TAC CTC ACG TGG GAT CGA GAC CAG TAT GAT AGG CTG  240
    Ala Tyr Leu Thr Trp Asp Arg Asp Gln Tyr Asp Arg Leu   80

    CCT GTG AAC ACC AAT GTG GTG CTG CGA TAT GAT GGG CTC  360
    Pro Val Asn Thr Asn Val Val Leu Arg Tyr Asp Gly Leu  120

    AAC CTG ACC TTT GGC TCC TGG ACC TAC AAT GGA AAC CAG  480
    Asn Leu Thr Phe Gly Ser Trp Thr Tyr Asn Gly Asn Gln  160

    GCT GTA AAG AAC GTC ATC TCC TAT GGC TGC TGC TCC GAG  600
    Ala Val Lys Asn Val Ile Ser Tyr Gly Cys Cys Ser Glu  200

    CTC ATA TCG TTC CTC GCT CCG TTG AGT TTC TAT CTC CCA  720
    Leu Ile Ser Phe Leu Ala Pro Leu Ser Phe Tyr Leu Pro  240
   ----------------MSR I--------------------------------
                                            ↓
    ATG CCA GCC TCA GAA AAT GTC CCT CTG ATA GGA AAA TAC  840
    Met Pro Ala Ser Glu Asn Val Pro Leu Ile Gly Lys Tyr  280
   --------                     ----------------------

    GCA CGG CCA GTG CCA CAC TGG GCC AAG GTG GTC ATC CTG  960
    Ala Arg Pro Val Pro His Trp Ala Lys Val Val Ile Leu  320

    GTC ACG AAG GTT TAT AGC AAA CTC CCA GAA TCC AAC CTG 1080
    Val Thr Lys Val Tyr Ser Lys Leu Pro Glu Ser Asn Leu  360

    ATC CCC CAG AAT ACT GAC AGT TAT TGT GCA CGC TAT GAA 1200
    Ile Pro Gln Asn Thr Asp Ser Tyr Cys Ala Arg Tyr Glu  400

    AAG GTC GCC AAA GTC ATA GAC CGT TTC TTC ATG TGG ATT 1320
    Lys Val Ala Lys Val Ile Asp Arg Phe Phe Met Trp Ile  440
    ---------------------------------------------------

    TTT AGA GAT TTG GGG AAA ACC CAA TAA AAT CAC CTG AGA 1440
                                                         457

    TCA ATA TCC TAG TTA CAT GTC AGG TTA AAT CAA GCA GGA 1560
    GGC CTT CAG TTT ATG TAA TTA TCT CTT TAT TAT TGT AGA 1680
    CTT TTT TTT TTA AAC AAA AAA AA                      1784
```

FIG. 1C

```
ALPHA1   STSSAVPLIGKYMLFTMVFVLASIIIIVIVDNTHHRSPSTEHLMPEWVRKVPIDTIPNIMPFSTMKRPSRIKQEKRIPTEDIIISDISGKPGPPMGPHE
ALPHA2   STSLVTPLIGEYLLFTLLFTIFVTLSIVIIVFVLANVHHRSPSTENMPNWVRVALLGRVPRWLM          MNRPLPMELHGSPDLKLSPSYEWLETNMDAGEREET
ALPHA3   STSLVTPLIGEYLLFTLLFTMIPFTLSIVIIVPVLANVHKRITPTEHTMPIWVTAVPLNLLPRVMF          MTRPTSGEGDTPKRITFYGAELSNLNCPSRADSKSCK
ALPHA4   STSLVTPLIGEYLLFTLLFTMIPFTLSIVIIVFVLANVHHRSPRTHTMPAWVRRVFLDIVPRLLP          MKRPSVVKDNCRLLIESMHTGANAPEWPEPVGEPGI
ALPHA7   ATSDSVPLIAQYFASTMITVGLSVVVFIVIVLERYTHHDPDGGKMPKWTRIILLNWCAWF               LRMKRPGEDKVRPACQHRPRPCSLASVELSAGAGPPTSN
ALPHA8   ATSDSVPLIAQYFASIMVTVGLSVVVFIVIVLV.QPHHHDPQAGKMAPFIWVRVILLNWCAW             PLRMKKPGENIKPLSCKYSYPKHPSLRNTEMNLPGHQP
ALPHA9   A.SENVPLIGKVYIATVALITAGPALHIMVMNIFCGAEARPVHWARVVILKYMSRILFVYDVGESCLSPRHSQEPEQVTKVYSKLPESNLKTSRNLDL
                                                        ─── MSR III ───

ALPHA4   LSDICNQGLSPAPTPCNFTDTAVETQPTCRSPPLEVPDLKTSEVEKASPCPSPGSCPPPKSSSGAPMLIKARSLSVQHVPSSQEAAEDGIRCRSRSIQYC
ALPHA1                                                                     SPLIKHPEVKSAIEGVKYTAETMKSDQESNNAAEPWK
ALPHA2   EE EEEEDENICVCAGLPDSSMGVLYGHGGLHLRAMEPETKTPSQASEILLSPQIQRALEGVHYTADRLRSEDADSVKEDWK
ALPHA3                                                                     EGYPCQDGTCGYCHERRVKISNFSANLTRSSSESVNAVLSLSALSPEIKEAIQSVKYTAENMKAQNVAKEIQDDWK
ALPHA7   VSQDGAASLADSKPTSSPTSLKARPSQLFVSDQASPCKCTCEEPSPVSPVTVLKAGGTKAPPQHLPLSPALTRAVEGVQYTAHLKABDTDPSVKEDWK
ALPHA8                                                                     GNLLYIGFRGLEGMHCAPTPDSGVVCGRLACSPTHDEEHLMHGAHPSDGDPDLAKILEEVRYTANRFRCQDESEVICSEWK
ALPHA9                                                                     SNGNMIYSYHTMENPCCPQNNDLGSKSGKITCPLSEDNEHVQRKALMDTIPVIVKILEEVQFTAMRFRKQDEGEEICSEWK
                                                                          SRKKEVRKLLRNDLGYQGGIPQNTDSYCARYEALAKNIEYTAKCLKDHRATNSKGSEWK

ALPHA1   YVAMVMDRILLGVEMIVCLIGLLAVPAGRLLIELHQOG
ALPHA2   YVAMVVDRIFLWLFIIVCFLGCLIGLPLPPFLAGMI
ALPHA3   YVAMVVIDRIPLWVEILVCILGAAGLPLQPLMARDET
ALPHA4   YVAMVVIDRIPLWMEIIVCLLGCLVGLPLPPWLAAC
ALPHA7   PAACVWDRLCLMAFSVFTIICILGILMSAPNFVEAVSKDFA
ALPHA8   PAAMVIDRLCLVAFTLPAIICFTILMSAPNFIEAVSKDFT
ALPHA9   KVAKVIDRFFMVIEFAMVFVMQIVLIIARAD
              ─── MSR IV ───
```

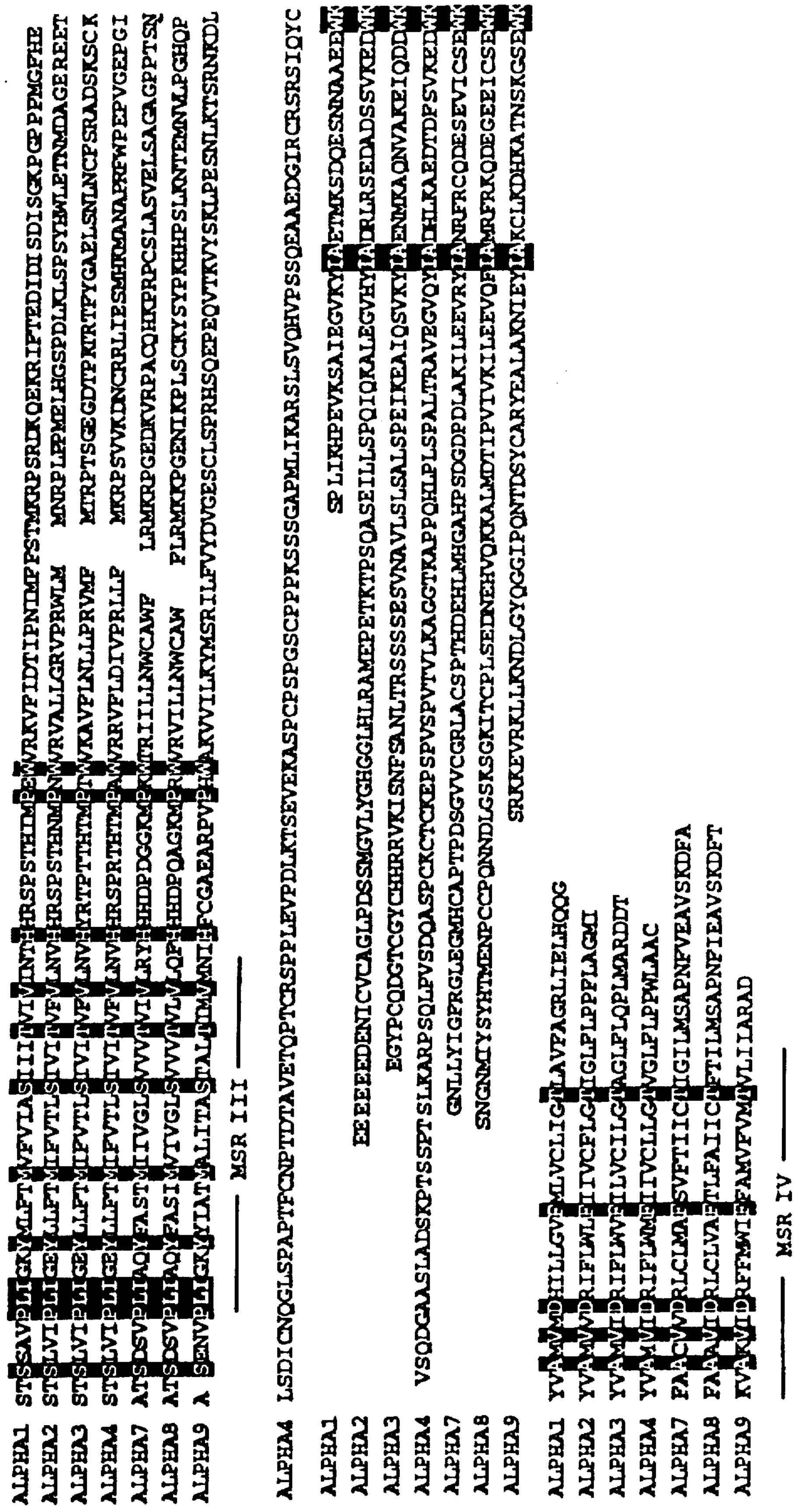

FIG. 3B

CLONING AND EXPRESSION OF A NOVEL ACETYLCHOLINE-GATED ION CHANNEL RECEPTOR SUBUNIT

This invention was made with Government support under Grant Number NS-11549, awarded by the National Institutes of Health. The Government has certain rights in this invention.

RELATED INVENTIONS

This invention is related to U.S. Ser. No. 07/898,185, filed Jun. 12, 1992, now U.S. Pat. No. 5,371,188, which is a continuation of U.S. Ser. No. 07/664,473, filed Mar. 4, 1991, now abandoned, which is, in turn, a continuation of U.S. Ser. No. 07/321,384, filed Mar. 14, 1989, now abandoned, which is, in turn, a continuation-in-part of U.S. Ser. No. 07/170, 295, filed Mar. 18, 1988, now abandoned, all of which are hereby incorporated by reference herein in their entirety.

BACKGROUND OF THE INVENTION

Intercellular communication is essential for the function of multicellular systems. Ion channel proteins, as mediators of information transfer in the brain, endocrine system, enteric nervous system and neuromuscular junction, modulate ion fluxes that produce voltage changes across cell membranes and simultaneously act as sensors of physiological signals, for example, changes in ligand concentrations and in transmembrane voltage. Ligand-gated ion channels provide for rapid dialogue between cells of the central nervous system, converting a chemical neurotransmitter signal released from one cell into an electrical signal that propagates along the cell membrane of a target cell. Ligand-gated ion channels are multimeric protein complexes with component subunits encoded by related genes.

At the present time, numerous families of ligand-gated receptors have been identified and characterized on the basis of sequence identity. Those which form cationic channels include, for example, excitatory nicotinic acetylcholine receptors (nAChRs), excitatory glutamate-activated receptors, the 5-$HT_3$ serotonin receptor, the ATP receptor and the sarcoplasmic ryanodine receptor. Those which form anionic channels include, for example, the inhibitory GABA and glycine-activated receptors.

The neurotransmitter acetylcholine (ACh) activates two pharmacologically different receptor types: nicotinic acetylcholine receptors (nAChR) from the ligand-gated ion channel superfamily and muscarinic acetylcholine receptors (mAChR) from the G-protein coupled receptor superfamily (Taylor, A. Goodman-Gilman, T. H. Rall, A. S. Nies and P. Taylor, eds. (New York:Pergamon Press), pp. 166–186, 1990); (Taylor, A. Goodman-Gilman, T. H. Rall, A. S. Nies and P. Taylor, eds. (New York:Pergamon Press), pp. 122–149, 1990). A number of pathologies and/or disease conditions are associated with nAChRs, such as, for example, myasthenia gravis, schizophrenia, Alzheimer's disease, Tourette's disease and nicotine addiction. Biochemical and electrophysiological data have shown that nicotinic and muscarinic receptors are functionally distinct entities. (Bonner, et al., *Science,* 237,527–532, 1987). Whereas nAChRs are pentamers composed of related protein subunits that span the plasma membrane four times, mAChRs are formed by a single polypeptide chain which is postulated to span the plasma membrane seven times.

Nicotinic acetylcholine receptors, glycoproteins composed of five subunits, transduce the binding of acetylcholine in the cationic channel. The five receptor subunits form a pseudosymmetric ring around a central channel. Neuronal nicotinic AChRs (NnAChRs) mediate neurotransmission at many central and peripheral synapses, and comprise two subunit types (alpha and beta) encoded by 10 different neuronal genes. Expression of particular combinations of subunit RNAs in oocytes yields biophysically distinct channels that are distinguished pharmacologically on the basis of ligands that modulate such channels.

Recombinant DNA technology has enabled the identification of the vertebrate muscle nAChR subunits alpha1, beta1, gamma, delta and epsilon and the neuronal subunits alpha2, alpha3, alpha4, alpha5, alpha6, alpha7, alpha8, beta2, beta3 and beta4 (rat nomenclature). Various combinations of these subunits produce functional recombinant receptor-channel complexes that are activated by both ACh and nicotine. The nAChR at the neuromuscular junction is thought to have a $(\alpha 1)_2\beta 1\gamma\delta$ stoichiometry (Galzi, et al., *Annu. Rev. Pharmacol.,* 31, 37–72, 1991). In contrast, the neuronal nAChR subunits alpha2, alpha3 and alpha4 lead to the assembly of functional nAChRs in concert with either beta2 or beta4 (Boulter, et al. *Proc. Natl. Acad. Sci. USA,* 84, 7763–7767, 1987; Ballivet, et al., *Neuron,* 1, 847–852, 1988; Wada, et al., *Science,* 240, 330–334, 1988; Deneris, et al., *Neuron,* 1, 45–54, 1988; Duvoisin, et al., *Neuron,* 3, 487–496, 1989; Couturier, et al., *J. Biol. Chem,* 265, 17560–17567, 1990), while the neuronal alpha7 and alpha8 subunits can form functional nAChRs in the absence of any other subunit (Couturier, et al., *J. Biol. Chem,* 265, 17560–17567, 1990; Seguela, et al., *J. Neurosci,* 13, 596–604, 1993; Gerzanich, et al., *Molec. Pharmacol.,* 45, 212–220, 1994).

Given the existence of ten distinct nicotinic acetylcholine subunit genes, numerous combinations of subunits producing functional receptors are possible. In spite of the numerous combinations of subunits which can be prepared from previously cloned genes, the properties of the native nAChRs do not always match those of recombinant receptors (Sargent, *Annu. Rev. Neurosci.,* 16, 403–443, 1993). For example, the cholinergic receptors present in bovine chromaffin cells and in rat and chick cochlear hair cells exhibit a pharmacological profile that does not fit any combination of known subunits (Shirvan, et al., *Proc. Natl. Acad. Sci. USA.,* 88, 4860–4864, 1991; Housley, et al., *Proc. R. Soc. Lond. B,* 244, 161–167, 1991; Fuchs, et al., *Proc. R. Soc. Lond. B,* 248, 35–40, 1992; Erostegui, et al., *Hearing Res.,* 74, 135–147, 1994), thus suggesting the existence of additional, as yet unidentified subunits.

Thus, a need exists for identifying additional members of the nicotinic acetylcholine receptor superfamily, and characterizing such nAChR subunits, as well as functional receptors assembled therefrom, which includes elucidation of the nature of assembly of various subunits in the production of a functional receptor (i.e., a subunit assembly containing ligand binding sites and a ligand-gated transmembrane channel), and the relationship between the structure of the subunit assembly and the pharmacological profile of the corresponding receptor. The present invention satisfies these needs and provides related advantages as well.

SUMMARY OF THE INVENTION

The present invention provides isolated nucleic acids encoding alpha9 nicotinic acetylcholine receptor (nAChR) subunit, isolated receptor subunit protein encoded thereby as well as recombinately expressed alpha9 nicotinic acetylcholine receptor (nAChR). Further provided are vectors and probes containing such nucleic acids, host cells transformed with such nucleic acids, antisense oligonucleotides and compositions containing such oligonucleotides, antibodies that specifically bind to invention receptors and compositions containing such antibodies as well as transgenic non-human mammals.

The alpha9 nAChR subunits of the invention form a cationic receptor channel complex which is activated by acetylcholine and is permeable to cations, including calcium. Functional alpha9 nACh receptors of the invention may be expressed as homomeric receptors, i.e., only one type of subunit is required for function, or invention receptors may be expressed as heteromeric receptors wherein more than one type of subunit is required to form a functional receptor. Additionally, the invention provides methods for identifying compounds that modulate activity of the invention receptors, or the activity of nucleic acid encoding such receptors.

BRIEF DESCRIPTION OF THE FIGURES

FIG. 1 shows the nucleotide and the amino acid sequence of the cDNA clone coding for the alpha9 nAChR subunit. The amino acid sequence is shown below the nucleotide sequence. Cleavage of the signal peptide is predicted at amino acid position 1 (Von-Heijne, *Nucl. Acid. Res.*, 14, 4683–4691, 1986). Amino acids encoding the signal peptide are assigned negative numbers. Nucleotides are numbered in the 5' to 3' direction, starting with the first nucleotide of the codon for the putative N-terminal residue of the mature protein. Nucleotides on the 5' side of amino acid residue 1 are indicated by negative numbers. Arrowheads indicate the intron location determined by genomic sequencing. Membrane spanning regions are underlined. The sequence information presented in FIG. 1 is also presented in Patentin format in SEQ ID NOs 1 and 2.

FIG. 4A shows current responses elicited by ACh, nicotine, muscarine, 1,1-dimethyl-4-phenylpiperazinium (DMPP), and oxotremorine-M (OXO-M) in oocytes injected with alpha9 cRNA and held at −50 mV under voltage-clamp.

FIG. 4B shows concentration-response curves to ACh, DMPP and OXO-M. Values represented are the mean and standard error of the mean of peak current values obtained in at least four oocytes per drug. Error bars are not shown when the standard error is smaller than the symbol. Responses from each cell were normalized to the maximal current evoked by ACh. The Hill equation ($EC_{50}$=9.7 μM; slope=1.3) was fitted to the ACh concentration-responsive curve.

In FIG. 7A the current-voltage relationship of ACh-evoked currents in alpha9-injected oocytes was determined by applying a voltage ramp (2 second duration, +50 mV to −120 mV) during the plateau phase of the current response. The traces are representative of those obtained in four different oocytes.

FIG. 7B shows representative current traces elicited by 100 μM ACh in alpha9-expressing oocytes before and after the injection of 50 nl of 20 mM 1,2-bis(2-aminophenoxy) ethane-N,N,$N^1$,$N^1$-tetraacetic acid (BAPTA).

FIG. 7C shows ACh-evoked currents in alpha9-injected oocytes held at −10 mV under voltage-clamp and bathed with a Ringer's solution containing 350 mM NaCl.

FIGS. 9A and 9B show the presence of alpha9 transcripts in the hypophyseal gland, the olfactory epithelium, the sternohyoid muscle and the tongue, of a rat embryo at stage E16. FIGS. 9C and 9D show a high magnification view of the pituitary in a rat embryo at stage E16 where alpha9 transcript is located in the pars tuberalis but not the pars distalis or the pars nervosa. FIGS. 9E and 9F show the presence of alpha9 transcripts in the pars tuberalis of the adult rat brain.

DETAILED DESCRIPTION OF THE INVENTION

Figures 2A, 2B:
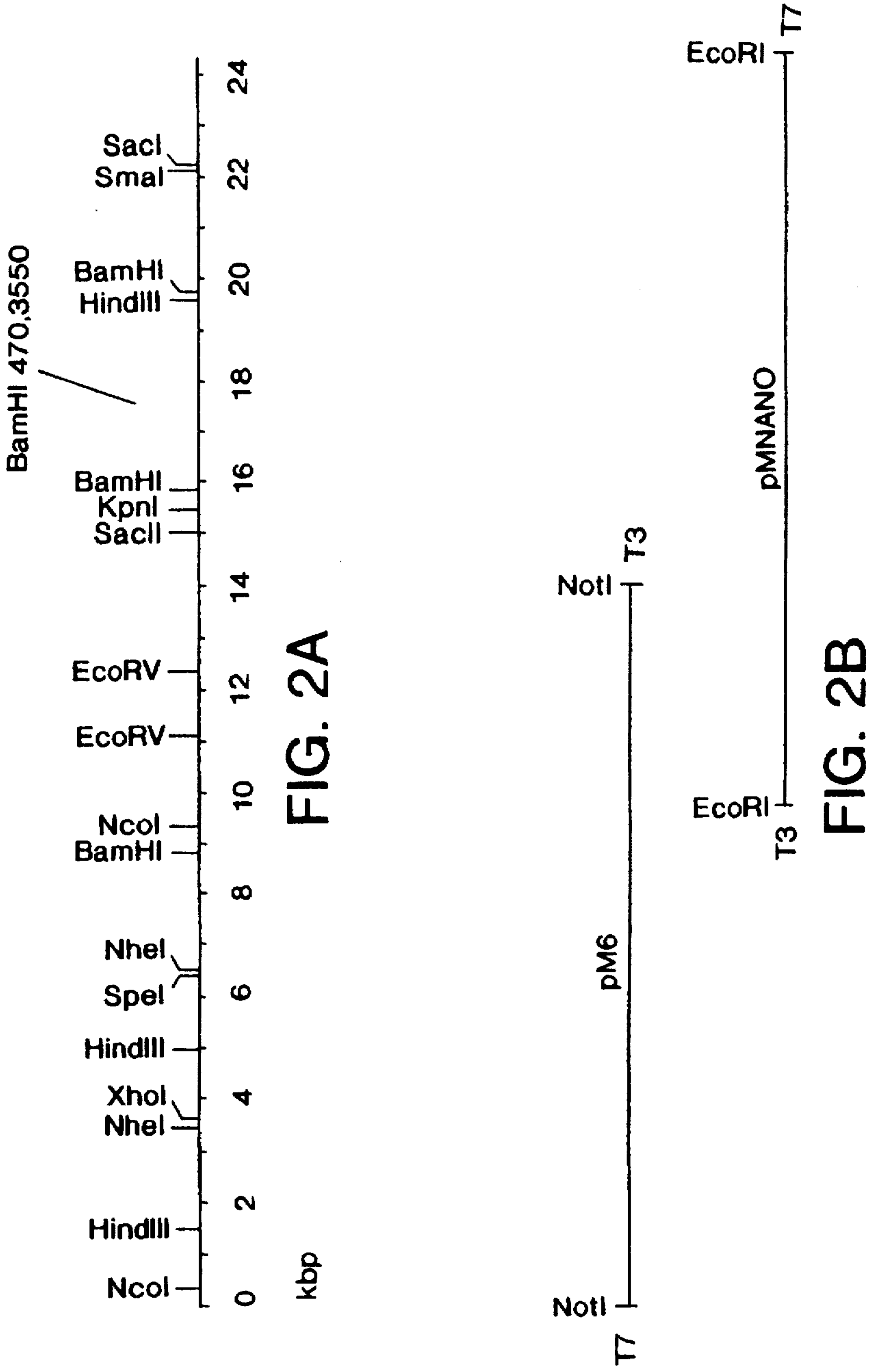
FIG. 2A shows the restriction map for the alpha9 subunit gene.
FIG. 2B shows a partial restriction map for overlapping genomic clones, M6 and MNANO, spanning the entire coding sequence of the alpha9 subunit gene. NcoI and NheI restriction sites not mapped in pMNANO, and SacI restriction sites are not mapped in pM6.

Molecular cloning studies have demonstrated structural and functional diversity in nicotinic acetylcholine receptors (nAChRs). To date, seven alpha subunits (alpha2 to alpha8) and three beta subunits (beta2 to beta4) have been characterized in the nervous system of vertebrates. The present invention describes the identification and functional characterization of a new member of this family of receptor subunit genes that are activated by the neurotransmitter acetylcholine (ACh). The new member is designated alpha9. The molecular structure of alpha9 indicates that it belongs to the ionotropic (nicotinic) rather than to the metabotropic (muscarinic) ACh receptor family. However, the mixed nicotinic-muscarinic properties of the recombinant alpha9 receptor differ from the pharmacological profile of all known functional nicotinic receptors.

Isolation and identification of the novel nAChR subunit gene of the present invention was accomplished by screening a rat genomic library using a rat nAChR alpha7 subunit cDNA as probe. DNA sequence analysis revealed that one isolated genomic clone encoded a protein with significant amino acid sequence identity with members of the ligand-gated ion channel gene superfamily. Its homology to known subunits revealed that it was more related to nAChR subunits than to $GABA_A$, glycine or 5-$HT_3$ receptor subunits. The presence of conserved contiguous cysteine residues in the extracellular domain, which are a hallmark of all nAChR alpha subunits and are thought to be part of the acetylcholine binding domain (Popot and Changeux, *Physiol. Rev.* 64, 1162–1193, 1984) suggested that this gene encoded a nAChR alpha subunit. Therefore, in accordance with current nomenclature, this newly discovered subunit has been designated the alpha9 subunit of the nAChR gene family.

A polymerase chain reaction (PCR) fragment derived from the isolated genomic clone was used to screen a rat olfactory epithelium cDNA library. Four independent cDNA clones were isolated, one of which contained a 1937 bp insert encoding an open reading frame for the alpha9 subunit. The nucleotide and deduced amino acid sequences are shown in FIG. 1 (and are also presented in Patentin format in SEQ ID NOs 1 and 2). The full length alpha9 cDNA encodes a mature protein of 451 amino acid residues, preceded by a leader sequence of 28 residues. It contains all the features characteristic of other members of the nAChR gene family, including four hydrophobic regions which predict potential membrane spanning regions, MSR I to IV (Kyte and Doolitle, *J. Mol. Biol.*, 157, 105–132, 1982), and cysteine residues at positions 127, 141, 191 and 192 (alpha9 numbering for the mature peptide, absent the 28 amino acid residues comprising the signal peptide) which are present in all nAChR alpha subunits.

The full-length alpha9 cDNA was used as a probe to screen two mouse genomic libraries constructed in phage vectors lambdaDASH II and lambdaFIX II. Two overlapping genomic clones were obtained (see FIG. 2). These clones, spanning the entire coding sequence of the alpha9 subunit gene, were cloned into plasmid vectors and the alpha9 subunit gene structure was determined by sequencing across the intron-exon boundaries. The intron-exon boundaries of the alpha9 gene are indicated in FIG. 1. The gene consists of five exons and has an intron-exon structure that differs from that of all known nAChR genes (Noda, et al., *Nature*, 305, 818–823, 1983; Nef, et al., *EMBO J.*, 7, 595–601, 1988; Wada, et al., *Science*, 240, 330–334, 1988; Buonanno, et al., *J. Biol. Chem.*, 264, 7611–7616, 1989; Boulter, et al., *J. Biol. Chem*, 265, 4472–4482, 1990). For example, in contrast to other nAChR subunit genes where the intron-exon boundaries of the first four exons are conserved, exons III and IV of the alpha9 gene are fused.

Figure 3A:
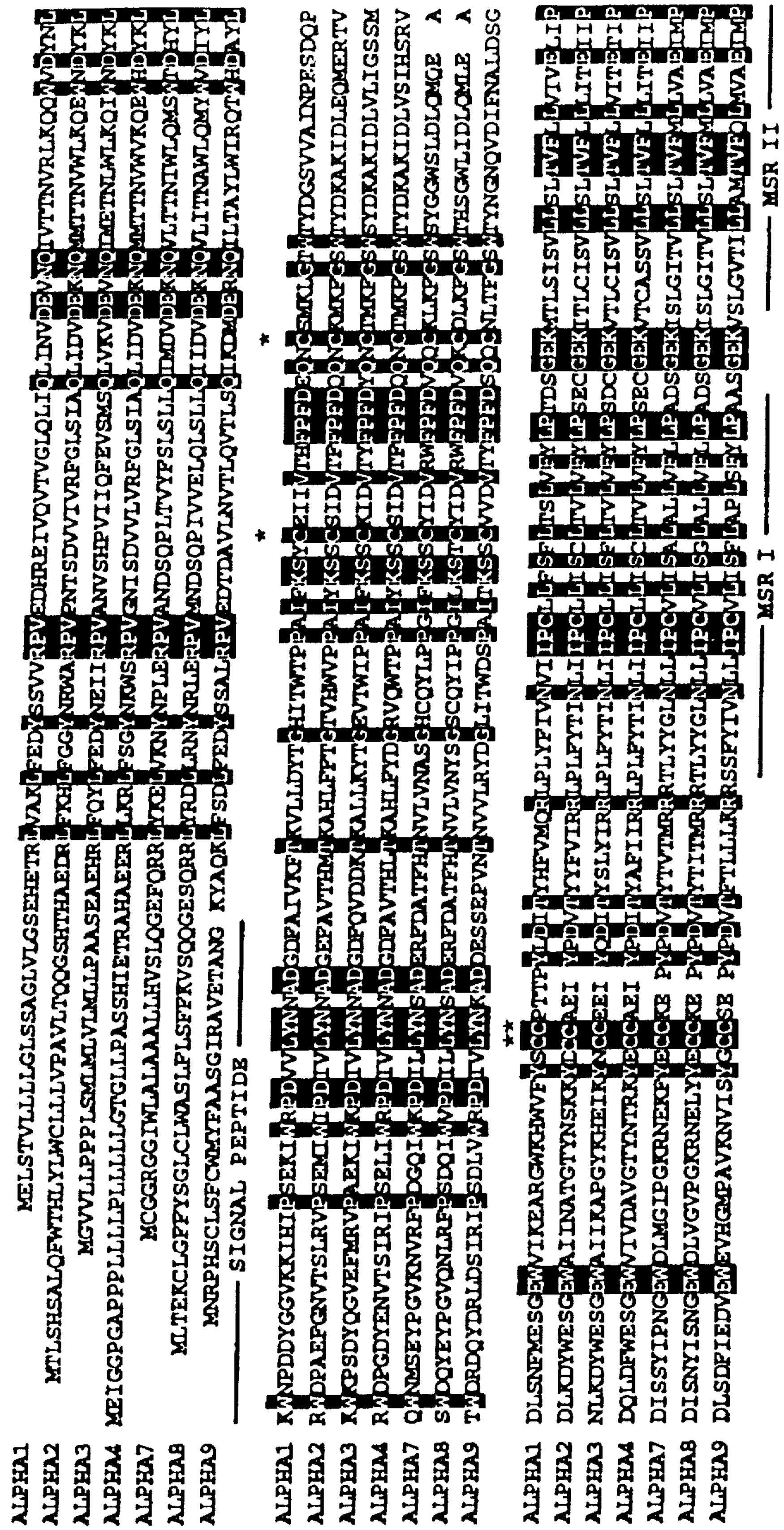
FIG. 3 shows the alignment of amino acid sequences for known nAChR alpha subunits. All sequences correspond to rat subunits, except for alpha8 which is a chick subunit. Identical residues in all sequences are presented as white letters in a black background. Spaces are introduced to maximize homologies. Predicted signal peptides and the four potential membrane spanning regions are indicated. Asterisks denote cysteine residues 127, 141, 191 and 192 (alpha9 numbering for the mature peptide, absent the 28 amino acid residues comprising the signal peptide) conserved in all nAChR alpha subunits. The sequence information presented in FIG. 3 is also presented in Patentin format n SEQ ID NOs 2–8.

The alpha9 cDNA clone was sequenced and the sequence compared with sequences of other nAChR alpha subunits (see FIG. 3). Based on sequence similarity, the alpha9 subunit appears to be a distant member of the nAChR subunit gene family. It is as distinct from the neuronal alpha7-alpha8 subfamily (38% amino acid sequence identity) as it is from the neuronal alpha2-alpha6 (36–39%) subfamily or from the muscle alpha1 subunit (37%). Although alpha9 shares the most highly conserved sequence elements with other members of the family, some amino acid residues differ from those found invariant in the other alpha subunits. For example, the conserved hydrophobic residues Phe-99 and Val-230 (alpha9 numbering for the mature peptide, absent the 28 amino acid residues comprising the signal peptide) are changed to the polar residues Ser-99 and Ser-230 in the alpha9 protein and the conserved positively charged residue Lys-144 is substituted by the non-charged residue Thr-144. The hydrophobic residues Leu-255 (alpha1-alpha6 subunits) or Met-255 (alpha7-alpha8 subunits) present in MSR II, are replaced by the polar amino acid Gln-255 in the alpha9 subunit. In addition, when compared to other nAChR subunits, alpha9 has a deletion of a Thr residue between MSR II and MSR III.

A full-length alpha9 cDNA suitable for Xenopus oocyte expression studies was constructed by subcloning the fragment from nucleotide −94 to 1766 (FIG. 1; i.e., residues 79 to 1938 as presented in SEQ ID NO:1) into the expression vector pGEMHE (Liman et al., *Neuron*, 9, 861–871, 1992). cRNA was synthesized using the mMessage mMachine transcription kit (Ambion, Austin, Tx.), with plasmid linearized with NheI.

Figure 4A:
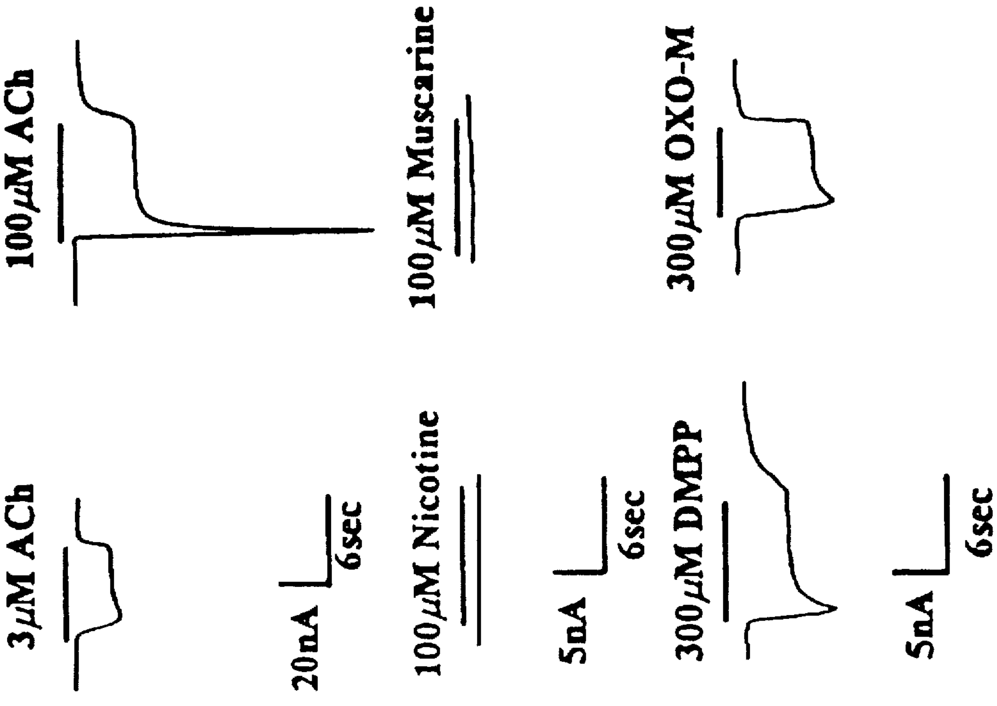
FIGS. 4A and 4B show electrophysiological responses of alpha9 injected oocytes to cholinergic agonists.

Two days after the injection of alpha9 cRNA, more than 95% of voltage-clamped Xenopus oocytes responded to acetylcholine. Inward currents in response to 100 μM acetylcholine ranged from 20 to 500 nA. FIG. 4A shows representative current traces in response to the application of acetylcholine. High concentrations (>10 μM) of this agonist evoked a fast peak response which rapidly decayed to a plateau level. Oocytes expressing alpha9 were insensitive to glutamate, GABA, glycine, serotonin, ATP, histamine and adenosine.

Figure 4B:
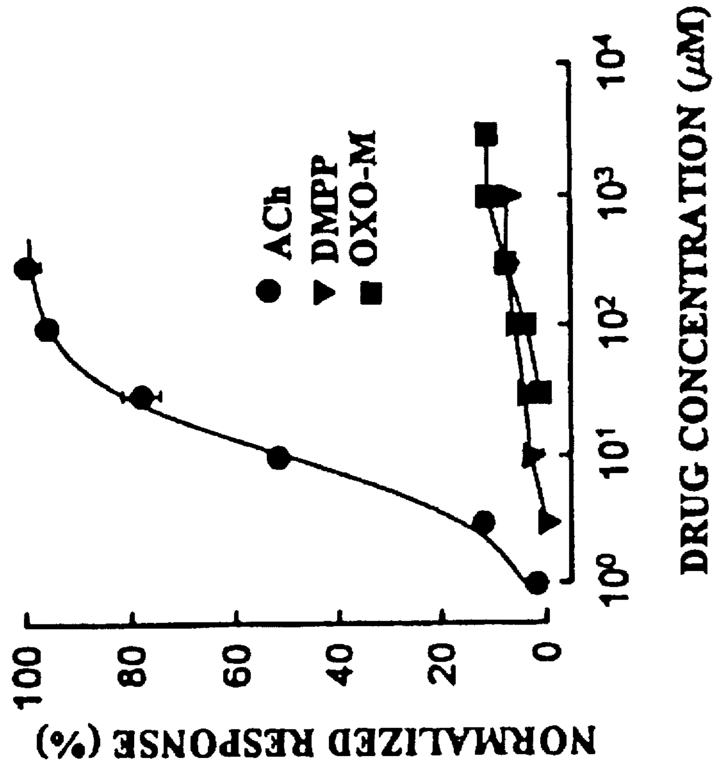

All functional nAChR alpha subunits cloned prior to the cloning of the alpha9 subunit, upon expression in Xenopus oocytes, form either heteromeric or homomeric receptor-channel complexes activated by nicotine (Boulter et al., *Proc. Natl. Acad. Sci. USA*, 84, 7763–7767, 1987; Duvoisin et al., *Neuron*, 3, 487–496, 1989; Couturier et al., *Neuron*, 5, 847–856, 1990; Luetje and Patrick, *J. Neurosci.* 11, 837–845, 1991; Seguela et al., *J. Neurosci.*, 13, 596–604, 1993; Gerzanich et al., *Molec. Pharmacol.*, 45, 212–220, 1994). Strikingly, nicotine (0.1 μM to 1 mM) did not elicit any response in alpha9-injected oocytes (FIG. 4A). Co-expression of alpha9 with either beta2 or beta4 nAChR subunits did not result in the formation of receptor-channels that were activated by nicotine. The alpha9 receptor-channel complex was also not activated by muscarine (FIG. 4A). Moreover, neither the nicotinic agonist cytosine nor the muscarinic agonists bethanecol and pilocarpine elicited current responses. However, both the nicotinic agonist 1,1-dimethyl-4-phenylpiperazinium (DMPP) and the muscarinic M1 agonist oxotremorine M (OXO-M), induced inward currents in alpha9-injected oocytes (FIG. 4A). FIG. 4B shows the concentration-response curves to these cholinergic agonists. Acetylcholine had an apparent affinity ($EC_{50}$) of 10 μM. The maximum current responses elicited by both DMPP and OXO-M were approximately 5% of that observed with acetylcholine.

Figure 5A:
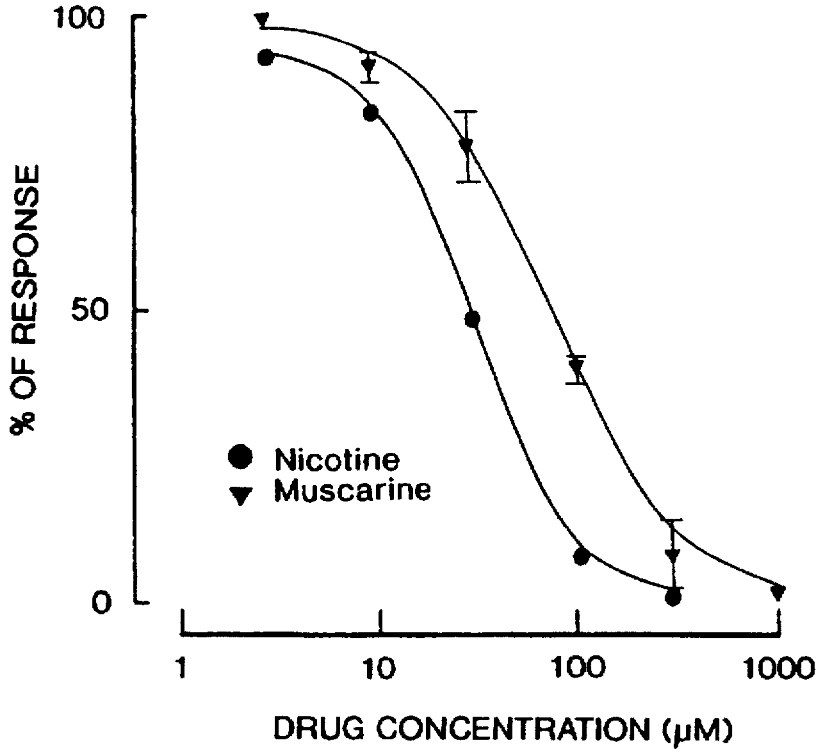
FIGS. 5A and 5B show the blockage of ACh responses in alpha9 injected oocytes by various antagonists. Inhibition curves were performed by the coapplication of 10 μM ACh and increasing concentrations of either (−) nicotine or (+) muscarine (see FIG. 5A) and strychnine, d-tubocurarine (d-TC) or atropine (see FIG. 5B). Responses are expressed as the percentage (%) of the control current evoked by 10 μM ACh. The mean and standard error of the mean of values obtained in at least four different oocytes per drug are shown. Error bars are not shown when the standard error is smaller than the symbol.
Figure 5B:
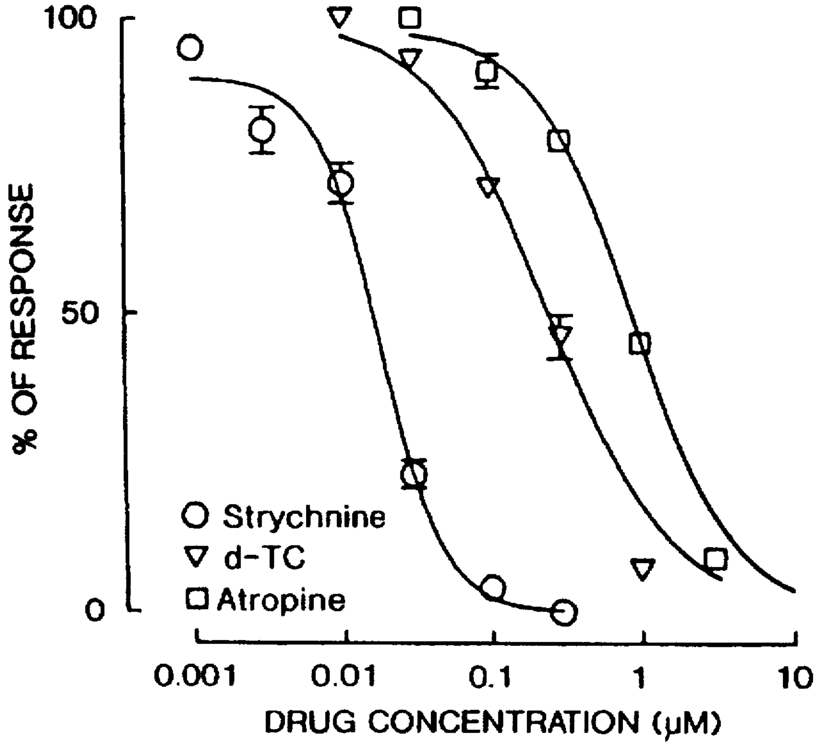
Figure 6A:
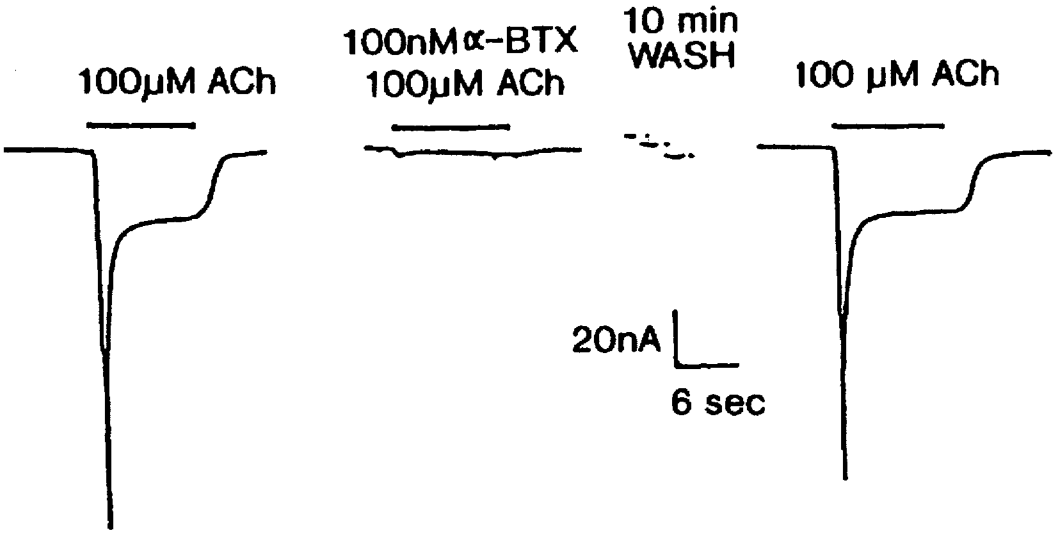
FIG. 6 shows the sensitivity of ACh-evoked currents in alpha9 injected oocytes to α- and κ-bungarotoxin. Representative current responses to 100 μM ACh recorded at a holding potential of −50 mV are shown. Oocytes were preincubated with α-bungarotoxin (α-BTX, A) or κ-bungarotoxin (κ-BTX, B) for 30 minutes before the application of the second test concentration of ACh.
Figure 6B:
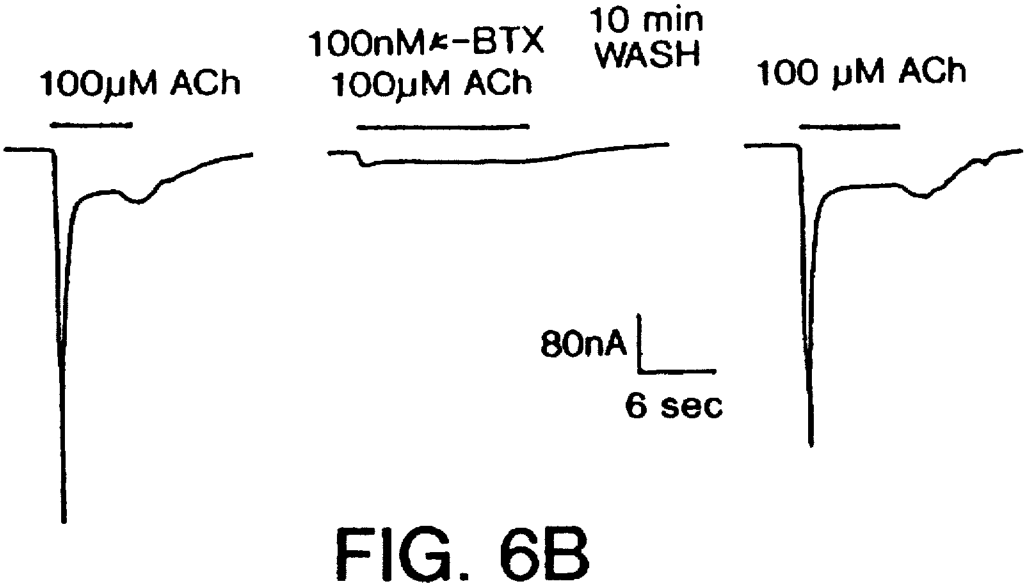

Although neither nicotine nor muscarine evoked responses in oocytes injected with alpha9 cRNA (see FIG. 4A), both of these classic cholinergic agonists reduced the currents evoked by acetylcholine. FIG. 5A shows the inhibition curves that resulted from the co-application of 10 μM acetylcholine with increasing concentrations of either nicotine or muscarine ($IC_{50}$=30 μM and 75 μM, respectively). As shown in FIG. 5B, the alpha9 receptor-channel complex was also blocked by the nicotinic antagonist d-tubocurarine ($IC_{50}$=0.3 μM), as well as by the muscarinic antagonist atropine ($IC_{50}$=1.3 μM). The alkaloid strychnine, classically used as a blocker of glycine-gated chloride channels, was found to be a potent antagonist of alpha9 homomers, with an $IC_{50}$ of 0.02 μM (FIG. 5B). Both α-bungarotoxin (100 nM) and κ-bungarotoxin (100 nM) blocked responses to 100 μM acetylcholine (FIG. 6). The blockade by these toxins was almost completely reversed after a 10 minute wash of the oocytes with frog Ringer's solution.

Figure 7A:
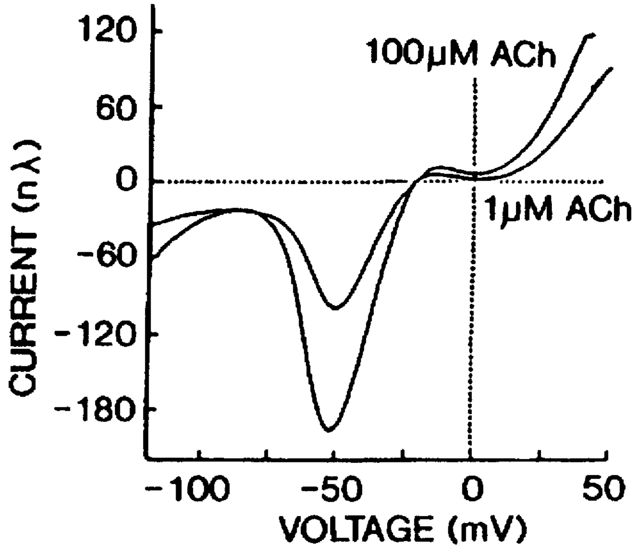
FIGS. 7A through 7C show the voltage-dependence of the ACh-evoked currents in alpha9 injected oocytes and $Ca^{2+}$ permeability of the recombinant alpha9 receptor.

Electrophysiological properties were determined on alpha9 injected oocytes 2–7 days after injection. The current-voltage (I-V) relationship obtained by the application of a 2 second voltage ramp at the plateau response to acetylcholine is shown in FIG. 7A. The I-V curve was non-linear, displaying a maximal inward current elicited by acetylcholine at −50 mV. Current responses were reduced at potentials negative to −50 mV. The fact that the ratio between the inward current elicited by 100 μM acetylcholine and that evoked by 1 μM acetylcholine was greater at −50 mV (2.1) than at −80 mV (1.0), indicates that the reduction in current responses at hyperpolarized potentials may depend upon agonist concentration. At holding potentials more positive than −50 mV, the inward currents activated by acetylcholine decreased until −25 mV, where a strong rectification was observed up to a holding potential of +20 mV. I-V curves for both peak and plateau responses performed with stepwise increments in the holding potential, had the same shape as shown in FIG. 7A.

Figure 7B:
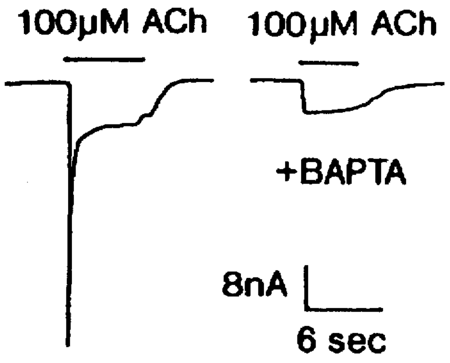
Figure 7C:
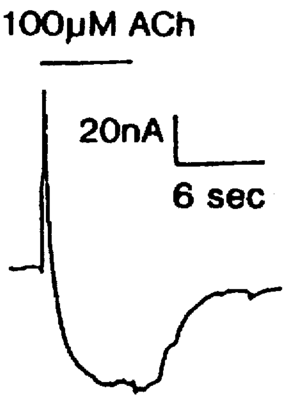

From the I-V relationships, an apparent reversal potential of −25 mV is estimated. This value is compatible with either a non-selective cationic current or with an anionic ($Cl^-$) current. The change in external NaCl concentration from 50 mM to 150 mM produced a positive shift in the reversal potential of acetylcholine-induced currents. This indicates that the alpha9 channel is permeable to $Na^+$. Most of the peak response elicited by 100 mM acetylcholine in alpha9-expressing oocytes disappeared when oocytes were injected with the calcium chelator 1,2-bis(2-aminophenoxy) ethane-N,N,$N^1$,$N^1$-tetraacetic acid (BAPTA) (see FIG. 7B). Thus, as has been suggested for other nAChR subunits (Gerzanich et al., *Molec. Pharmacol.*, 45, 212–220, 1994), this result indicates that part of the current evoked by acetylcholine is carried by a $Cl^-$ current through $Ca^{2+}$ activated $Cl^-$ channels known to be present in oocytes (Miledi and Parker, *J. Physiol.* (*Lond*)., 357, 173–183, 1984). In order to further test the participation of a $Ca^{2+}$ activated $Cl^-$ current in response to acetylcholine, the reversal potentials of $Cl^-$ and $Na^+$ were shifted in opposite directions by transiently raising the external NaCl concentration to 350 mM and holding the oocytes at −10 mV under two electrode voltage clamp. Under this condition, 100 μM acetylcholine elicited both an outward current followed by an inward current (FIG. 7C). As reported for other neuronal nAChRs (Vernino et al., *Neuron*, 8, 127–134, 1992; Seguela et al., *J. Nerousci.*, 12, 596–604, 1993), the inward current probably results from the influx of cations through alpha9 receptor-channels and the outward current from the flux of $Cl^-$ through $Ca^{2+}$-activated $Cl^-$ channels. It should be noted that I-V curves performed in 1,2-bis(2-aminophenoxy)ethane N,N,$N^1$,$N^1$-tetraacetic acid injected oocytes had the same shape as that described above, suggesting that the $Cl^-$ current did not contribute to the I/V curve under the conditions of the experiment.

The above-described Xenopus oocyte expression studies demonstrate that the alpha9 protein subunit forms ion channels activated by acetylcholine and permeable to both $Na^+$ and $Ca^{2+}$. Similar to the alpha7 and alpha8 neuronal subunits (Couturier et al., *Neuron*, 5, 847–856, 1990; Gerzanich et al., *Molec. Pharmacol.*, 45, 212–220, 1994), alpha9 can assemble into a homomeric receptor-channel complex. This differs from other functional neuronal nAChR alpha subunits which require co-assembly with a beta subunit in order to form receptor-channel complexes (Boulter et al., *Proc. Natl. Acad. Sci. USA*, 84, 7763–7767, 1987; Ballivet et al., *Neuron*, 1, 847–852, 1988; Wada et al., *Science*, 240, 330–334, 1988).

Currents elicited by acetylcholine in alpha9-injected oocytes decreased at holding potentials negative to −50 mV. This could result from a voltage-dependent blockade of the channel either by acetylcholine or by cations present in the solution used to maintain the oocytes. The fact that the block was more pronounced at high agonist concentrations indicates that at least part of this effect is due to a voltage-dependent channel block by acetylcholine. High concentrations of acetylcholine and carbamylcholine are known to produce a voltage- and concentration-dependent channel block of muscle nAChR present in $BC_3H$-1 cells (Sine and Steinbach, *Biophys. J.*, 46, 277–284, 1984).

Based on its primary structure and electrophysiological properties, the alpha9 protein belongs to the nicotinic family of ligand gated ion channels which includes subunits for nAChR, $GABA_A$, glycine and 5-$HT_3$ receptors. However, as described earlier, in alpha9-injected oocytes, nicotine, muscarine, d-tubocurarine and atropine blocked acetylcholine-evoked current responses. Therefore, the alpha9 receptor-channel complex falls into neither the nicotinic nor the muscarinic subdivisions of the pharmacological classification scheme of cholinergic receptors (P. Taylor in The pharmacalogical basis of therapeutics, A. Goodman-Gilman, T. H. Rall, A. S. Nies and P. Taylor, eds. (New York:Pergamon Press), pp. 122–149 and 166–186, 1990). The finding that both the nicotinic agonist DMPP and the muscarinic agonist OXO-M are capable of eliciting current responses in alpha9-injected oocytes indicates that the alpha9 receptor exhibits a mixed nicotinic-muscarinic pharmacology. In addition, the blockage of alpha9 receptors by the glycine receptor antagonist strychnine is unusual. A similar effect of strychnine has also been reported on alpha7 and alpha8 homomers expressed in Xenopus oocytes (Seguela et al., *J. Neurosci.*, 12, 596–604, 1993; Gerzanich et al., *Molec. Pharmacol.*, 45, 212–220, 1994).

The alpha9 protein subunit contains the most conserved amino acid residues within the proposed acetylcholine binding site of nAChR alpha subunits (Dennis et al., *Biochem*, 27, 2346–2357, 1988; Galzi et al., *J. Biol. Chem.*, 265, 10430–10437, 1990). Nevertheless, two non-conservative substitutions in the alpha9 protein, Phe-99 to Ser and Lys-144 to Thr (position numbers refer to the mature protein, absent the 28 residues of the leader sequence), are near the first and second domains of the postulated agonist binding site for nAChR. These amino acid substitutions are likely to be responsible for the distinct pharmacological properties of the alpha9 receptor-channel complex.

Figure 9A:
FIGS. 9A through 9F show the results of in situ hybridization of sagittal sections of rat embryos and coronal sections of adult brains and identification and transcript localization of alpha9.
Figure 9B:
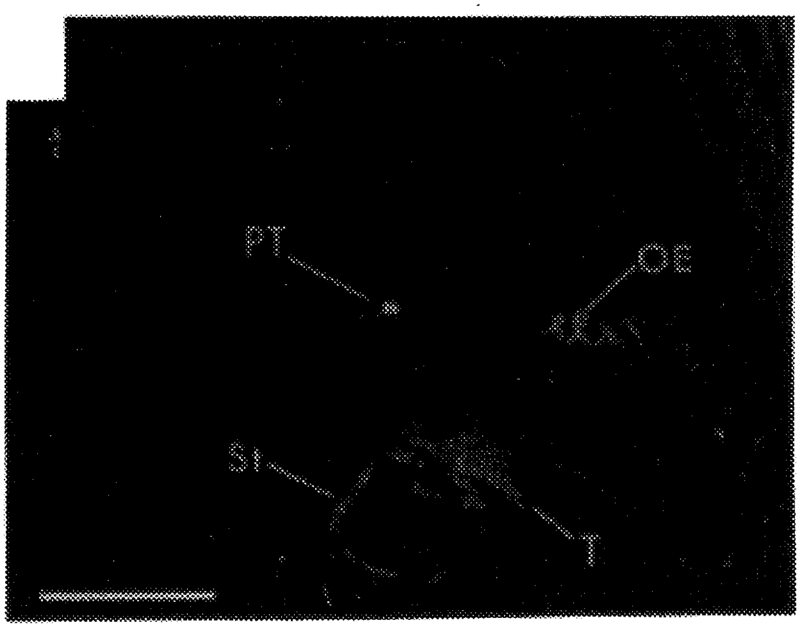
Figure 9C:
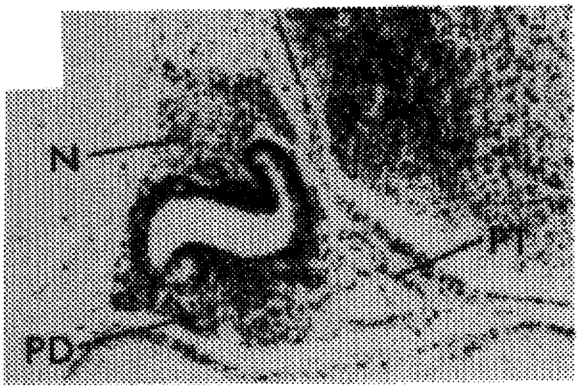
Figure 9D:
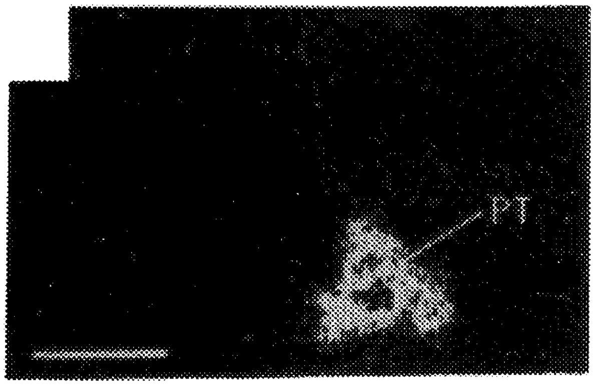
Figure 9E:
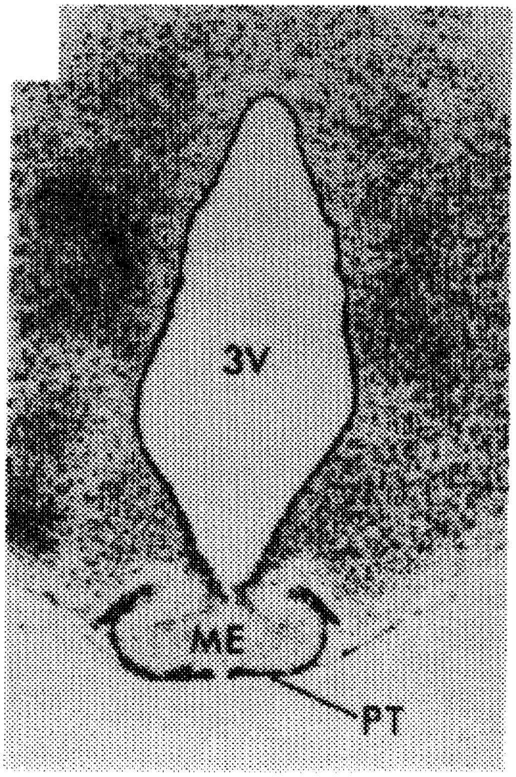
Figure 9F:
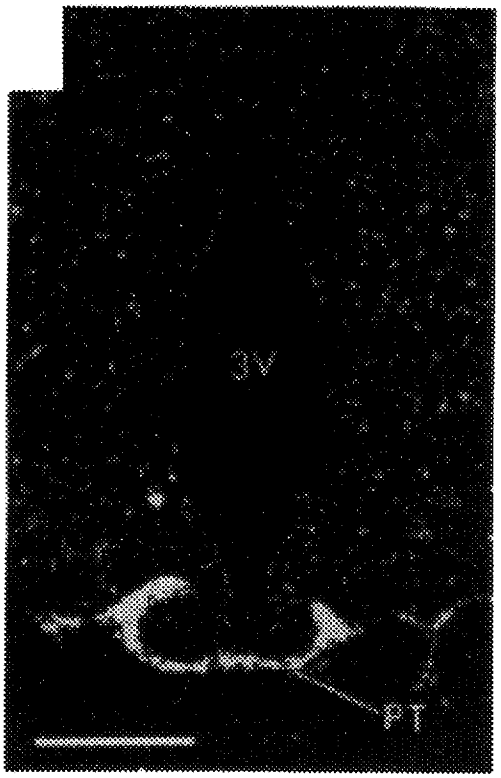

To determine the tissue expression pattern of the alpha9 gene, in situ hybridization studies were performed. In vitro synthesized RNA derived from coding sequence of the alpha9 genomic clone was hybridized to sagittal sections of rat embryos and coronal sections of adult rat brains. The presence of transcripts are observed in the hypophyseal gland of a rat embryo at stage E16 (see FIGS. 9B and 9D). The alpha9 gene expression is observed to be restricted to the pars tuberalis of the adenohypophysis, whereas the pars distalis and the neurohypophysis show no detectable signal. The alpha9 mRNA is also observed to be present in the adult rat pars tuberalis, at the ventral surface of the median eminence (see FIG. 9F). Alpha9 expression is also observed throughout the E16 rat olfactory mucosa (see FIG. 9B). The alpha9 transcripts are detected in the pseudostratified columnar epithelium that lines each of the turbinates of the olfactory organ. Additional expression is seen in the tongue of the developing rat (FIG. 9B). Finally, in situ hybridization analysis performed on 20 mm coronal sections every 180 mm throughout the adult brain, did not establish alpha9 gene expression in the central nervous system of the rat.

In situ hybridization studies performed on cryostat sections of the rat cochlea indicate that the alpha9 gene is also expressed in the outer hair cell region of all cochlea turns. No expression of the alpha9 gene was observed in spiral ganglion neurons or other supporting structures of the cochlea (see FIG. 9B).

Previously published neuronal nAChR genes are reported as being expressed in the central nervous system of vertebrates (Sargent, *Annu. Rev. Neurosci.*, 16, 403–443, 1993). As disclosed above, in situ hybridization studies performed in coronal sections throughout the rat brain did not establish alpha9 gene expression in the central nervous system. Although low levels of alpha9 transcripts or a very restricted expression pattern which escaped detection cannot be ruled out, the results suggest that relative to other nAChR subunits, alpha9 may be involved in a distinct subset of cholinergic functions in vivo. In situ hybridization studies showed that in the rat the alpha9 subunit gene is expressed in the pars tuberalis of the pituitary, the olfactory epithelium, the outer hair cells of the cochlea and the skeletal muscle of the tongue.

The pars tuberalis constitutes an anatomically well defined part of the vertebrate adenohypophysis consisting of peptide-secreting cells, gonadotropes and thyrotropes (Wittkowski et al., *Acta Endocrinol.*, 126, 285–290, 1992). Neuroendocrine effects, such as the inhibition of luteinizing hormone and thyroid-stimulating hormone secretion in response to nicotine exposure, has been reported in humans and rats (Fuxe et al., *Psychoneuroendocrinol.*, 14, 19–41, 1989). Although these effects have been attributed to the activation of hypothalamic nAChR, the presence of the alpha9 nAChR subunit in the pituitary indicates that nicotine may exert a direct action on this gland.

It is likely that the olfactory sensory cells receive efferent innervation that modulates olfactory function (Shirley, *Olfaction. Intl. Rev. Neurobiol.*, 33, 1–53, 1992). A cholinergic modulation has been suggested, since the application of acetylcholine causes slow electrical potentials and modifies spike activity in olfactory receptor neurons (Bouvet et al., *Neurosci. Res.*, 5, 214–223, 1988). Although further pharmacological characterization of the acetylcholine response in olfactory neurons as well as a more precise localization of the alpha9 subunit within the olfactory epithelium are necessary, the presence of alpha9 transcripts in the olfactory epithelium could provide the molecular basis for the cholinergic effect described.

The alpha9 gene expression in the developing muscle of the tongue is intriguing. With the in situ hybridization studies performed it is not possible to distinguish whether the signal is actually localized in muscle fibers or in the surrounding connective tissue. However, alpha9 transcripts appear not to be present in all developing skeletal muscles. For example, in situ hybridization studies performed in mid-sagittal sections of rat embryos showed no evidence of alpha9 transcripts in the intercostal or axial muscles.

The overall pharmacological characteristics of the homomeric alpha9 receptor expressed in oocytes differ from those of other cloned nAChRs (Boulter, et al., *Proc. Natl. Acad. Sci. USA*, 84, 7763–7767, 1987; Ballivet, et al., *Neuron*, 1, 847–852, 1988; Wada, et al., *Science*, 240, 330–334, 1988; Couturier, et al., *Neuron*, 5, 847–856, 1990; Gerzanich, et al., *Molec. Pharmacol.*, 45, 212–220, 1994).

Figure 8:
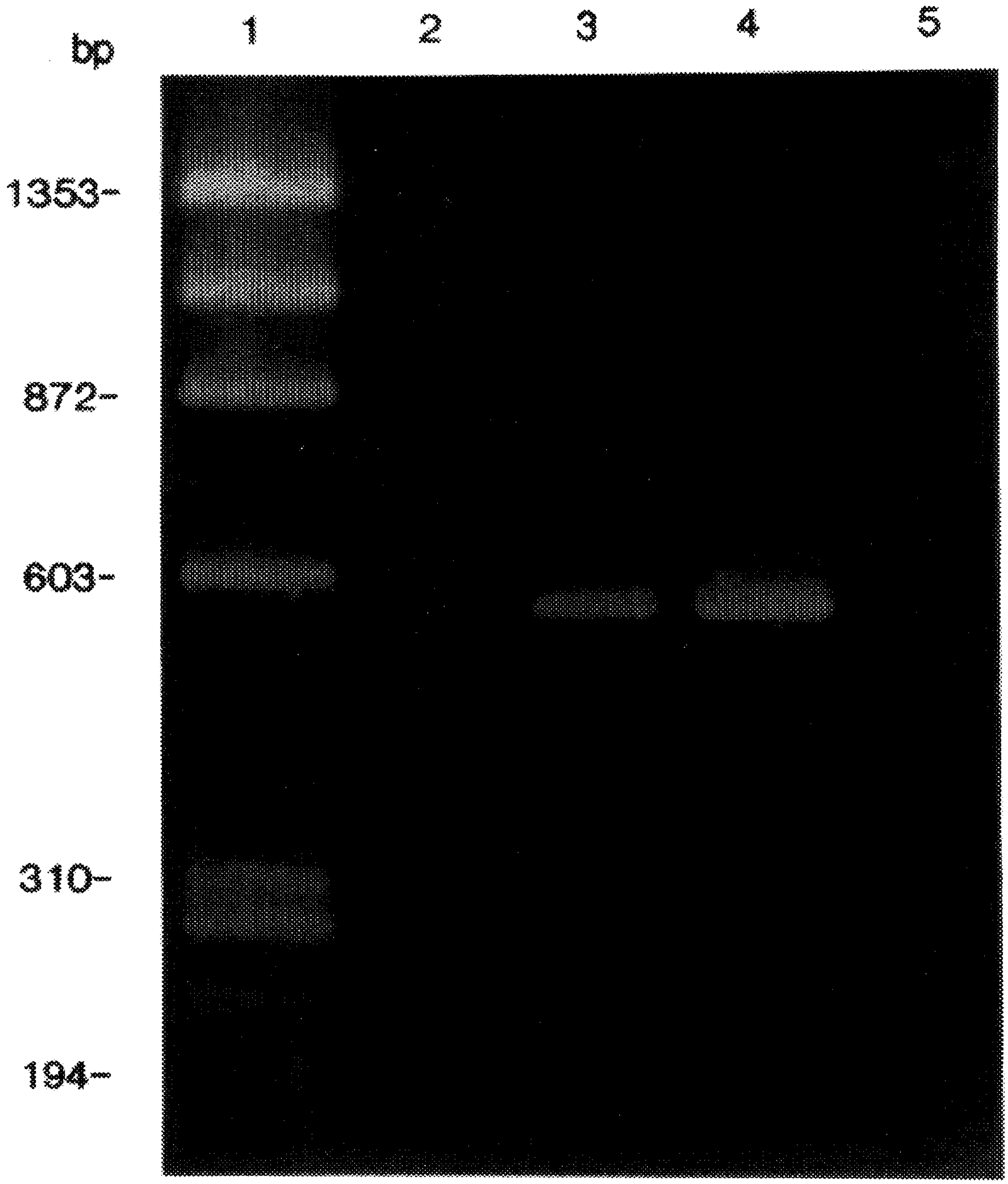
FIG. 8 shows detection of alpha9 transcripts in the rat cochlea. Amplification reactions were performed as described in Example VI, using cDNA transcribed from total RNA as template and alpha9 specific primers. Resolution of the amplified products in a 1.5% agarose gel stained with ethidium bromide is shown. An aliquot of 10 μM of each reaction mixture was loaded per lane. Lane 1, DNA ladder; lane 2, no DNA template; lane 3, amplified product from olfactory epithelium cDNA; lane 4, amplified product from olfactory epithelium cDNA; lane 5, amplified product from sciatic nerve cDNA.

In order to further investigate the expression pattern of the alpha9 gene in the rat cochlea, PCR was performed on cDNA reverse transcribed from cochlear total RNA. Two primers specific for the alpha9 sequence were designed and used to amplify a fragment that spans an intron-exon boundary of the alpha9 gene. As shown on FIG. 8, a fragment of the expected size (573 bp) was amplified from rat cochlear cDNA with alpha9 primers. Restriction endonuclease analysis of the fragment with AccI, HinfI and NcoI, further confirmed that it was derived from alpha9 transcripts. Since the alpha9 gene is also transcribed in the rat olfactory epithelium, RNA obtained from this tissue was used as a positive control. Rat sciatic nerve cDNA was included as a negative control to rule out the possibility that, with the parameters used for the PCR, very low levels of transcripts would be detected in any tissue studied. Whereas no DNA was amplified from the sciatic nerve using specific primers for alpha9 (see FIG. 8), both alpha3 and alpha4 subunits could be detected in this tissue with their respective specific primers.

A possible physiological role for the alpha9 receptor-channel is the efferent cholinergic innervation of cochlea hair cells. Outer hair cells of the cochlea are implicated in the mechanical amplification of sound in vertebrates (Flock, R. Klinke and R. Hartmann, eds. (Berlin:Springer-Verlag), pp. 2–8, 1983). These cells receive efferent cholinergic innervation. The electrical stimulation of these efferent neurons results in reduction of sensitivity and tuning of the auditory nerve fibers, which in turn could induce protection against acoustic trauma (Brown and Nuttal, *J. Physiol. (Lond.)*, 354, 625–646, 1984; Klinke, *Hearing Res.*, 22, 235–243, 1986; Rajan and Johnstone, *Brain Res.*, 458, 241–255, 1988). The molecular nature of the acetylcholine receptor involved in the efferent innervation of cochlear hair cells has not been described. Although both a non-selective cation channel as well as a G-protein coupled receptor have been proposed, cholinergic agonists and antagonists have been of little benefit to characterize this receptor as either nicotinic or muscarinic (Housley and Ashmore, *Proc. R. Soc. Lond. B*, 244, 161–167, 1991; Fuchs and Murrow, *Proc. R. Soc. Lond. B*, 248, 35–40, 1992; Fuchs and Murrow, *J. Neurosci.*, 12, 800–809, 1992; Kakehata et al., *J. Physiol. (Lond.)*, 463, 227–244, 1993; Erostegui et al., *Hearing Res.*, 74, 135–147, 1994). Therefore, whatever the primary structure for this cholinergic receptor might be, based on its unique pharmacological characteristics it has been suggested that it is of a receptor type not previously described (Fuchs and Murrow, *Proc. R. Soc. Lond. B*, 248, 35–40, 1992; Erostegui et al., *Hearing Res.*, 74, 135–147, 1994).

The results presented herein suggest that the alpha9 receptor is the cholinergic component of the cochlear efferent system. This conclusion is based primarily on the presence of alpha9 transcripts in the hair cells of the rat cochlea. Evidence to date suggests that the cochlear efferent system is involved in improving the detection of signal within background noise, protection of the cochlea from noise damage, and attenuating the cochlear response to auditory stimulation when attention must be focused elsewhere.

Various experiments have shown that the cholinergic component of the cochlear efferent system may also be involved in aminoglycoside antibiotic ototoxicity. When administered in high doses, these antibiotics cause outer hair cells (OHC) to degenerate (Govaerts, et al., *Toxicology Letters,* 52, 227–251, 1990). The results of such degeneration ranges from ringing in the ears to total loss of hearing. Current theories regarding the mechanisms whereby aminoglycosides exert their ototoxic effect upon the OHCs suggest that the OHCs become metabolically destabilized due to a block of intracellular messaging systems. At the same time, the efferent synapses are also destabilized, and can no longer monitor and control the amount of ACh released following stimulation. The end result is that there is an overstimulation (an excess of ACh) directed toward the destablized OHCs, which results in the degeneration observed (Williams, et al., *Hearing Res.,* 30, 11–18, 1987). Thus, ACh, and the alpha9 receptor responsible for transducing the efferent signal from the efferent terminal to the hair cell, are intimately involved in releasing the ototoxic potential of the aminoglycoside antibiotics. Accordingly, antagonists to receptors comprising at least one alpha9 receptor subunit (i.e., alpha9 blockers) will reduce or eliminate the side-effects of aminoglycoside-induced ototoxicity.

The present invention provides isolated nucleic acids encoding an alpha9 nicotinic acetylcholine receptor subunit. The term "nucleic acids" (also referred to as polynucleotides) encompasses RNA as well as single and double-stranded DNA and cDNA. As used herein, the phrase "isolated polynucleotide" refers to a polynucleotide that has been separated or removed from its natural environment. One means of isolating a polynucleotide encoding an alpha9 nAChR receptor subunit is to probe a mammalian genomic library with a DNA probe using methods well known in the art. DNA probes derived from the alpha9 receptor gene particularly useful for this purpose. DNA and cDNA molecules that encode alpha9 receptors can be used to obtain complementary genomic DNA, cDNA or RNA from human, mammalian, or other animal sources. Such molecules can also be used to isolate related cDNA or genomic clones by screening cDNA or genomic libraries, by methods described in more detail below. Invention nucleic acids include nucleotide sequences that are substantially the same as the nucleotide sequence shown in FIG. 1 (see also SEQ ID NO:1). The present invention also encompasses nucleic acids which are degenerate variants of the nucleotide sequence shown in FIG. 1 (and SEQ ID NO:1).

The term "degenerate variants" refers to nucleic acids encoding alpha9 nAChR subunits that, by virtue of the degeneracy of the genetic code, do not necessarily hybridize to the invention nucleic acids under specified hybridization conditions. Preferred nucleic acids encoding invention polypeptide(s) or proteins(s) are comprised of nucleotides that encode substantially the same amino acid sequence set forth in FIG. 1 (see also SEQ ID NO:2). Alternatively, preferred nucleic acids encoding invention polypeptide(s) hybridize under high stringency conditions to substantially the entire sequence, or substantial portions (i.e., typically at least 25–30 contiguous nucleotides) of the nucleotide sequence set forth in FIG. 1 (see also SEQ ID NO:1).

Stringency of hybridization, as used herein, refers to conditions under which polynucleotide hybrids are stable. As known to those of skill in the art, the stability of hybrids is a function of sodium ion concentration and temperature. (See, for example, Sambrook et al., *Molecular Cloning: A Laboratory Manual* 2d Ed. (Cold Spring Harbor Laboratory, 1989; incorporated herein by reference).

The invention provides isolated alpha9 nicotinic acetylcholine receptor subunit peptide, polypeptide and/or protein encoded by invention nucleic acids and alpha9 nicotinic acetylcholine receptor comprising said subunit. The alpha9 nAChR subunit comprises a protein of approximately 451 amino acids in length. The amino acid sequence of the alpha9 subunit is set forth in FIG. 1 (and in SEQ ID NO:2).

As used herein, the term "isolated protein" refers to a protein free of cellular components and/or contaminants normally associated with a protein in its native in vivo environment. Invention polypeptides and/or proteins include naturally occurring allelic variants, as well as recombinant forms thereof. The alpha9 nAChR polypeptide can be isolated using various methods well known to those of skill in the art. The methods available for the isolation and purification of invention proteins include, precipitation, gel filtration, ion-exchange, reverse-phase and affinity chromatography. Other well-known methods are described in Deutscher et al., *Guide to Protein Purification: Methods in Enzymology* Vol. 182, (Academic Press, 1990), which is incorporated herein by reference. Alternatively, isolated polypeptides of the present invention can be obtained using well-known recombinant methods as described, for example, in Sambrook et al., *Molecular Cloning: A Laboratory Manual* 2d Ed. (Cold Spring Harbor Laboratory, 1989; incorporated herein by reference).

Invention polypeptide(s) can be produced by expressing nucleic acids encoding the alpha9 nAChR subunit in a suitable host cell, such as a bacterial cell, a yeast cell, an amphibian cell (i.e., oocyte), or a mammalian cell, using methods well known in the art. The expressed polypeptide can be recovered using well-known methods. Invention polypeptides can be isolated directly from cells that have been transformed with expression vectors, described below in more detail. The invention polypeptide, biologically active fragments, and functional equivalents thereof can also be produced by chemical synthesis. As used herein, "biologically active fragment" refers to any portion of the alpha9 polypeptide represented by the amino acid sequence in FIG. 1 (see also SEQ ID NO:2) that can assemble into a cationic channel activated by acetylcholine and permeable to calcium. Synthetic polypeptides can be produced, for example, using Applied Biosystems, Inc. Model 430A or 431A automatic peptide synthesizer (Foster City, Calif.) employing the chemistry provided by the manufacturer.

As used herein, the phrase "nicotinic acetylcholine receptor (nAChR) subunit" refers to recombinantly expressed/produced (i.e., isolated or substantially pure) protein that contains four highly hydrophobic regions which predict membrane spanning regions and cysteine residues at positions 127, 141, 191 and 192 (referring to the mature peptide, not including the 28 amino acid leader sequence). Such protein subunits assemble into a cationic channel which is activated by acetylcholine. Invention nAChR subunits include variants thereof encoded by mRNA generated by alternative splicing of a primary transcript, as well as biologically active fragments.

The alpha9 nAChR subunit of the invention contributes to the formation of a functional receptor, as assessed by methods described herein, by combining with at least one additional nAChR subunit of the same or different type. As used herein, the phrase "functional receptor" means that the binding of a ligand, for example, acetylcholine (ACh), causes the receptor ion channel to open thereby permitting cations, such as $Ca^{2+}$, as well as $Na^+$ and $K^+$, to enter the cell. Agonist activation of a "functional invention receptor" induces the receptor.

Modification of invention nucleic acids, polypeptides or proteins with the following phrases: "recombinantly expressed/produced", "isolated", or "substantially pure", encompasses nucleic acids, peptides, polypeptides or proteins that have been produced in such form by the hand of man, and are thus separated from their native in vivo cellular environment. As a result of this human intervention, the recombinant nucleic acids, polypeptides and proteins of the invention are useful in ways that the corresponding naturally occurring molecules are not, such as identification of compounds as potential drugs.

Sequences having "substantial sequence homology" are intended to refer to nucleotide sequences that share at least about 90% identity with invention nucleic acids; and amino acid sequences that typically share at least about 95% amino acid identity with invention polypeptides. It is recognized, however, that polypeptides or nucleic acids containing less than the above-described levels of homology arising as splice variants or generated by conservative amino acid substitutions, or by substitution of degenerate codons are also encompassed within the scope of the present invention.

The present invention also provides nucleic acids encoding alpha9 receptor subunit(s) operatively linked to a promoter, as well as other regulatory sequences. As used herein, the phrase "operatively linked" refers to the functional relationship of the nucleic acid with regulatory and effector sequences, such as promoters, enhancers, transcriptional and translational stop sites, and other signal sequences. Specifically operative linkage of a nucleic acid to a promoter refers to the physical and functional relationship between the nucleic acid and the promoter such that transcription of DNA is initiated from the promoter by an RNA polymerase that specifically recognizes and binds to the promoter.

Suitable promoters include specific sequences that are sufficient for RNA polymerase recognition, binding and transcription initiation. Additionally, suitable promoters include sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, and the like.

Vectors employed in the present invention contain both a promoter and a cloning site into which nucleic acid encoding alpha9 receptor subunit(s) can be operatively linked. Such vectors, which are well known in the art, are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potentially inappropriate alternative translation initiation codons or other sequences that may interfere with or reduce expression, either at the level of transcription or translation. Alternatively, consensus ribosome binding sites can be inserted immediately 5' of the start codon to enhance expression. (See, for example, Kozak, *J. Biol. Chem.* 266:19867 (1991)). Similarly, alternative codons, encoding the same amino acid, can be substituted for native codons of the alpha9 nAChR subunit in order to enhance transcription (e.g., the codon preference of the host cell can be adopted, the presence of G-C rich domains can be reduced, and the like).

Examples of suitable vectors that may be employed in the present invention include viruses, such as baculoviruses and retroviruses, bacteriophages, cosmids, plasmids and other recombination vehicles typically used in the art. Invention nucleic acids are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic linkers can be ligated to the termini of restricted invention nucleic acids. These synthetic linkers contain nucleic acid sequences that correspond to a particular restriction site in the vector DNA. Additionally, a nucleic acid containing a termination codon and an appropriate restriction site can be ligated into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

Also provided are vectors comprising nucleic acid encoding alpha9 nAChR subunit, which vectors are adapted for expression in a bacterial cell, a yeast cell, an amphibian cell (i.e., oocyte), a mammalian cell or other animal cells. Such vectors additionally comprise regulatory elements necessary for expression of nucleic acid in the bacterial, yeast, amphibian, mammalian or animal cells located relative to the nucleic acid encoding alpha9 nAChR subunit so as to permit expression thereof. As used herein, "expression" refers to the process by which nucleic acids are transcribed into mRNA and translated into peptides, polypeptides, or proteins. If the nucleic acid is derived from genomic DNA, expression may include splicing of the mRNA, if an appropriate eucaryotic host is selected. Regulatory elements required for expression include promoter sequences to bind RNA polymerase and transcription initiation sequences for ribosome binding. For example, a bacterial expression vector might include a promoter such as the lac promoter, the Shine-Dalgarno transcription initiation sequence and the start codon AUG (Sambrook et al., *Molecular Cloning: A Laboratory Manual* 2d Ed. (Cold Spring Harbor Laboratory, 1989; incorporated herein by reference). Similarly, a eucaryotic expression vector might include a heterologous or homologous promoter for RNA polymerase II, a downstream polyadenylation signal, the start codon AUG, and a termination codon for detachment of the ribosome. Such vectors can be obtained commercially or assembled from available sequences and by methods well known in the art.

This invention also provides a transformed host that expresses recombinant alpha9 nicotinic acetylcholine receptor. Such a host has been transformed with a nucleic acid encoding alpha9 nAChR subunit. An example of a transformed host according to the present invention is a mammalian cell comprising a plasmid specifically adapted for expression in such a cell. The plasmid contains a nucleic acid encoding an alpha9 nAChR subunit and the regulatory elements necessary for expression of the subunit. Suitable mammalian cells that may be utilized in the present invention include, for example, mouse fibroblast NIH3T3 cells, CHO cells, HeLa cells, $Ltk^-$ cells, PC12 and N2A neuronal cells, HEK-293 kidney cells and CG4 glial cells. Host cells may be transformed with plasmids such as those described supra by methods well known in the art such as calcium phosphate precipitation, DEAE-dextran, electroporation, microinjection or lipofection. Other suitable hosts that may be employed in the present invention are oocytes, particularly Xenopus oocytes.

Nicotinic acetylcholine receptors, according to the invention, are recombinantly expressed in a host cell containing at least one alpha9 subunit. Recombinant receptors may be homomeric or heteromeric. Thus, a transformed host cell can recombinantly express a receptor containing only alpha9 subunits, or containing at least one alpha9 subunit and one or more other nAChR subunits.

The present invention also provides nucleic acid probes. Such probes comprise a polynucleotide capable of specifically hybridizing with a sequence encoding an alpha9 nAChR subunit. As used herein, the term "probe" refers to single-stranded or double-stranded DNA or RNA that has a sequence of nucleotides that includes at least 14 contiguous bases set forth in FIG. 1 (see also SEQ ID NO:1). Probes used to distinguish the alpha9 subunit from other alpha nAChRs subunits will preferably consist of at least 14 contiguous bases from the cytoplasmic loop region of the alpha9 nucleotide sequence. Alternatively, probes that are to be used to find additional subunits of the nAChR family will preferably consist of at least 14 contiguous bases from a membrane spanning region of the alpha9 nucleotide sequence.

As used herein, the phrase "specifically hybridizing" encompasses the ability of a polynucleotide to recognize a nucleic acid sequence that is complementary thereto and to form double-helical segments via hydrogen bonding between complementary base pairs. Nucleic acid probe technology is well known to those skilled in the art who will readily appreciate that such probes may vary greatly in length and may be labeled with a detectable agent, such as a radioisotope, a fluorescent dye, and the like, to facilitate detection of the probe. Invention probes are useful to detect the presence of nucleic acids encoding the alpha9 nAChR subunit. For example, the probes can be used for in situ hybridizations to identify specific tissues in which the alpha9 nAChR subunit gene is expressed. Additionally, oligonucleotides complementary to nucleic acids encoding the alpha9 nAChR subunit are useful for detecting the alpha9 gene and associated mRNA, or for the isolation of related genes using homology screening of genomic or cDNA libraries, or by using amplification techniques well known to those of skill in the art.

The invention further provides antisense oligonucleotides having a sequence capable of binding specifically with any portion of an mRNA that encodes the alpha9 nAChR subunit so as to prevent translation of the mRNA. Antisense oligonucleotides may also contain a sequence capable of binding specifically with any portion of the cDNA encoding the alpha9 subunit. As used herein, the phrase "binding specifically" encompasses the ability of a nucleic acid sequence to recognize a complementary nucleic acid sequence and to form double-helical segments therewith via the formation of hydrogen bonds between the complementary base pairs.

Also provided by the present invention are compositions comprising an amount of an invention antisense oligonucleotide effective to reduce expression of the alpha9 nAChR subunit wherein said antisense oligonucleotide is capable of binding with mRNA encoding the alpha9 nAChR receptor so as to prevent its translation. Compositions provided by the present invention comprise an acceptable hydrophobic carrier capable of passing through cell membranes and may also comprise a structure which binds to a receptor specific for a selected cell type and is thereby taken up by cells of the selected cell type. The structure may be part of a protein known to bind to a cell-type specific receptor.

Antisense oligonucleotide compositions (AOCs) according to the present invention are designed to be stable in the blood stream for administration to a subject by injection, or in laboratory cell culture conditions. The physical and chemical properties of the AOC are selected so that the composition is capable of passing through the cell membrane in order to enter the cell cytoplasm. Such a composition can be designed to include small, hydrophobic chemical structures, or alternatively, specific cell transport systems which facilitate and transport the AOC into the cell. In addition, the AOC can be designed for administration only to certain selected cell populations by targeting the AOC to be bound and taken up by select cell populations. Targeting can be accomplished by designing cell specific AOCs to bind to a receptor found only in a certain cell type, as discussed supra. Alternatively, an AOC can also be designed to recognize and selectively bind to a target mRNA sequence. In the latter instance, targeting is accomplished, for example, by employing a sequence contained within the sequence shown in FIG. 1 (SEQ ID NO:1). The AOC is designed to inactivate the target mRNA sequence by (1) binding to target mRNA and inducing degradation of the mRNA by, for example, RNase I digestion, or (2) inhibiting translation of target mRNA by interfering with the binding of translation-regulating factors or ribosomes, or by inclusion of other chemical structures, such as ribozyme sequences or reactive chemical groups which either degrade or chemically modify the target mRNA. AOCs have been shown to be capable of such properties when directed against mRNA targets (see Cohen et al., *TIPS*, 10:435 (1989) and Weintraub, *Sci. American*, January (1990), pp. 40; both incorporated herein by reference).

The invention also provides antibodies having specific reactivity with alpha9 nAChR polypeptides and/or proteins of the subject invention. Active fragments of antibodies are encompassed within the definition of "antibody".

The antibodies of the invention can be produced by methods known in the art. For example, polyclonal and monoclonal antibodies can be produced by methods described, for example, in Harlow and Lane, *Antibodies: A Laboratory Manual* (Cold Spring Harbor Laboratory 1988), which is incorporated herein by reference. The alpha9 protein of the invention, or portions thereof, can be used as the immunogen in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding alpha9 invention protein. Altered antibodies such as chimeric, humanized, CDR-grafted or bifunctional antibodies can also be produced by methods well known in the art. Such antibodies can also be produced by hybridoma, chemical synthesis or recombinant methods described, for example, in (Sambrook et al., *Molecular Cloning: A Laboratory Manual* 2d Ed. (Cold Spring Harbor Laboratory, 1989); incorporated herein by reference and Harlow and Lane, supra). Both anti-peptide and anti-fusion protein antibodies can be used. (see, for example, Bahouth et al., *Trends Pharmacol. Sci.* 12:338 (1991); Ausubel et al., *Current Protocols in Molecular Biology* (John Wiley and Sons, NY 1989) which are incorporated herein by reference).

The invention antibodies have various uses, such as, for example, isolation of the alpha9 invention receptor.

Additionally, the antibodies are useful for detecting the presence of the alpha9 receptor, as well as analysis of receptor localization, subunit composition, and structure of functional domains. A method for detecting the presence of alpha9 nAChRs on the surface of a cell comprises contacting the cell with an antibody that specifically binds alpha9 nACh receptor and detecting the presence of the bound antibody on the cell surface. With respect to the detection of alpha9 receptors, the invention antibodies can be used, for example, for in vitro diagnostic or in vivo imaging methods.

Immunological procedures useful for in vitro detection of alpha9 receptor in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

Further, invention antibodies can be used to modulate the ion channel activity of the alpha9 receptor in animals and humans as well as biological tissues isolated therefrom. Accordingly, the invention provides compositions comprising a carrier and an amount of an antibody having specificity for the alpha9 receptor effective to block binding of naturally occurring ligands to the receptor. A monoclonal antibody directed to an epitope of an alpha9 receptor present on the surface of a cell wherein said antibody has an amino acid sequence substantially the same as an amino acid sequence set forth in Sequence ID No. 2 can be useful for this purpose.

The invention further provides a transgenic non-human mammal capable of expressing nucleic acid encoding alpha9 protein. Also provided are transgenic non-human mammals incapable of expressing nucleic acid encoding biologically functional alpha9 protein or alternatively, capable only of expressing alpha9 protein that is biologically deficient in some respect. Varying degrees of disfunctionality are achieved through manipulation of alpha9 nucleic acid to encode a mutated protein.

The present invention also provides a transgenic non-human mammal having a genome comprising antisense nucleic acid which is transcribed into antisense mRNA complementary to alpha9 mRNA. Such antisense mRNA hybridizes to alpha9 mRNA and reduces the translation thereof.

Nucleic acids employed in transgenic animals of the invention may be associated with an inducible promoter and/or tissue specific regulatory elements, so that expression can be induced, or restricted to specific cell types. Examples of suitable promoters are the metallothionein promoter and the L7 promoter.

The transfer of nucleic acid material into mammalian hosts for the purpose of generating transgenic animals can be accomplished by microinjection, retroviral infection or other means well known to those skilled in the art, of the material into appropriate fertilized embryos. (See, for example, Hogan et al., *Manipulating the Mouse Embryo: A Laboratory Manual* (Cold Spring Harbor Laboratory, 1986). Homologous recombination can also be used for the generation of transgenic animals according to the present invention. Homologous recombination techniques are well known in the art. Homologous recombination replaces a native (endogenous) gene with a recombinant or mutated gene to produce an animal that cannot express a native (endogenous) alpha9 receptor subunit but can express, for example, a mutated receptor subunit. In contrast to homologous recombination, microinjection adds genes to the host genome, without removing host genes. Microinjection can produce a transgenic animal that is capable of expressing both endogenous and exogenous alpha9 receptor subunits. Transgenic animal model systems are useful for in vivo screening of compounds for identification of receptor-specific ligands, i.e., agonists and antagonists, which activate or inhibit receptor responses.

Nucleic acids, oligonucleotides (including antisense), vectors containing same, transformed hosts, receptor subunits and combinations thereof, as well as antibodies of the present invention, can be used to screen compounds in vitro to identify those compounds which function as agonists or antagonists of alpha9 receptor subunits of the invention. Such in vitro screening assays provide useful information regarding the function and activity of alpha9 receptor subunits of the invention, which can facilitate the identification and design of drugs that are capable of specific interaction with one or more types of receptor subunits or receptor subtypes.

The present invention also provides a method for identifying compounds which bind to alpha9 nicotinic acetylcholine receptor subunits. In such a method, invention receptor subunits may be employed in a competitive binding assay. Such an assay can accommodate the rapid screening of a large number of compounds to determine which compounds, if any, are capable of binding to the alpha9 nAChR subunit. Subsequently, more detailed assays can be carried out with those compounds found to bind, to further determine whether such compounds act as agonists or antagonists of invention receptors (i.e., nAChRs comprising at least one alpha9 subunit).

The present invention still further provides a bioassay for identifying compounds which modulate the activity of receptors of the invention (i.e., nAChRs comprising at least one alpha9 subunit). In one embodiment, the bioassay is conducted by providing cells expressing receptor comprising at least one alpha9 subunit with at least one potential agonist and thereafter monitoring the cells for changes in ion channel activity. In yet another embodiment, the bioassay is conducted by contacting cells expressing receptor comprising at least one alpha9 subunit with a constant amount of a known alpha9 agonist and increasing amounts of at least one potential antagonist and thereafter monitoring the cells for changes in ion channel activity.

The present invention also provides a bioassay for identifying compounds which modulate the regulatory regions of the alpha9 nAChR subunit gene. Such an assay is conducted utilizing mammalian cells transformed with a nucleic acid construct comprising at least a portion of the regulatory region of the alpha9 gene operatively associated with a reporter gene. The transformed cells are contacted with at least one compound wherein the ability of said compound to modulate the regulatory region is unknown. Thereafter, the cells are monitored for expression of the reporter gene. Suitable reporter genes that may be employed include, for example, the chloramphenicol acetyltransferase gene, the luciferase gene, and the like.

A compound or a signal that "modulates the activity" of an invention receptor refers to a compound or a signal that alters the activity of the alpha9 receptor so that the receptor is different in the presence of the compound or signal than in the absence of the compound or signal. Compounds affecting modulation include agonists and antagonists. An agonist encompasses a compound such as acetylcholine, that activates alpha9 receptor function. Alternatively, an antagonist includes a compound that interferes with alpha9 receptor function. Typically, the effect of an antagonist is observed as a blocking of agonist-induced receptor activation. Antagonists include competitive as well as non-competitive antagonists. A competitive antagonist (or competitive blocker) interacts with or near the site specific for agonist binding. A non-competitive antagonist or blocker inactivates the function of the receptor by interacting with a site other than the agonist interaction site.

As understood by those of skill in the art, bioassay methods for identifying compounds that modulate nAChR activity generally require comparison to a control. One type of "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture that can be employed is a cell or culture that is identical to transfected cells, with the exception that the "control" cell or culture does not express functional alpha9 nACh receptor subunit. Accordingly, the response of the transfected cell to compound is compared to the response (or lack thereof) of the "control" cell or culture to the same compound under the same reaction conditions.

In still another embodiment of the present invention, the ion channel activity of alpha9 nAChR can be modulated by contacting the receptors with an effective amount of at least one compound identified by any of the above-described bioassays.

The following examples are intended to illustrate, but not limit, the present invention.

EXAMPLE I

Screening of Genomic Libraries

A full-length alpha7 nAChR subunit cDNA (Seguela, et al., *J. Neurosci.*, 13, 596–604, 1993) was used to screen $5\times10^5$ clones of a lambdaCharon 4A rat genomic library (obtained from Dr. James Eberwine, Department of Pharmacology, University of Pennsylvania Medical School, Philadelphia, Pa.). Hybridization was carried out at 65° C. in 1M NaCl, 50 mM Tris-HCl, pH 8.0, 0.5% SDS, 100 mg/ml denatured salmon sperm DNA and 0.1% (w/v) each of Ficoll, polyvinylpyrrolidone and bovine serum albumin. Filters were washed at 45° C. in 2×SSPE (1×SSPE is 180 mM NaCl, 9 mM $Na_2HPO_4$, 0.9 mM $NaH_2PO_4$ and 1 mM EDTA, pH 8.0). A clone of ~16 kb containing exons IV and V of the alpha9 subunit gene was isolated.

EXAMPLE II

Screening of a cDNA Library

A PCR fragment derived from coding sequences (nucleotides 283 to 806, FIG. 1; i.e., nucleotides 455 to 979 of SEQ ID NO:1) of the rat genomic clone described in EXAMPLE I was used as a probe to screen $1\times10^6$ plaques of a lambdaNM1149 adult rat olfactory epithelium cDNA library (obtained from Dr. Heinz Breer, and Dr. Klaus Raming, University Stuttgart-Hohenheim, Institute of Zoophysiology, Stuttgart, Germany). Hybridization was as described in EXAMPLE I and filters were washed at 65° C. in 0.2×SSPE. Four independent clones were isolated, one contained a full-length alpha9 cDNA (FIG. 1). The alpha9 cDNA consists of an 87 bp 5' untranslated region, an open reading frame of 1437 bp and 413 bp of 3' untranslated region. The full length alpha9 cDNA was used as a probe to screen two mouse (129SvJ) genomic libraries constructed in phage vectors lambda DASHII and lambda FIXII. Two overlapping genomic clones were obtained (FIG. 2). These clones, spanning the entire coding sequence of the alpha9 subunit gene were cloned into plasmid vectors and the alpha9 subunit gene structure was determined by sequencing across the intron-exon boundaries.

EXAMPLE III

Nucleotide Sequence Determination and Analysis

The alpha9 subunit cDNA clone was sequenced using the Sequenase 2.0 kit (United States Biochemical, Cleveland, Ohio) and synthetic oligonucleotide primers. A comparison of the alpha9 amino acid sequences with other nAChR alpha subunits was made using sequence analysis software from the University of Wisconsin Genetics Computer Group [Devereux, et al., *Nucl. Acids. Res.*, 12, 387–395, 1984]. The percent sequence identity between paired sequences was calculated by dividing the number of identical residues by the total number of residues in the shorter of the sequences and multiplying the quotient by 100.

EXAMPLE IV

Electrophysiological Procedures

A full-length alpha9 cDNA suitable for Xenopus oocyte expression studies was constructed by subcloning the fragment from nucleotide −94 to 1766 (FIG. 1; i.e., residues 79 to 1938 as presented in SEQ ID NO:1) into the expression vector pGEMHE (Liman, et al., *Neuron*, 9, 861–871, 1992). cRNA was synthesized using the mMessage mMachine transcription kit (Ambion, Austin, Tx.), with plasmid linearized with NheI.

The isolation and maintenance of oocytes has been previously described (Boulter, et al., *Proc. Natl. Acad. Sci. USA*, 84, 7763–7767, 1987). Each oocyte was injected with 1 to 10 ng of cRNA. Electrophysiological recordings were performed 2 to 7 days after injection, under two-electrode voltage clamp with an Axoclamp 2A amplifier (Axon Instruments, Foster City, Calif.). Voltage electrodes were filled with 3M KCl and had a resistance of ~10 MΩ; current electrodes were filled with 0.3M KCl and had a resistance of ~1 MΩ. Unless otherwise stated, the holding potential was −50 mV. I-V relationships were obtained with pClamp 5.5 software (Axon Instruments), by applying 2 second voltage ramps in the presence of agonist and subtracting the control average values obtained before and after agonist application. All records were digitized and stored on a computer. Data was analyzed using software that was designed and provided by Dr. S. Traynelis (The Salk Institute for Biological Studies, La Jolla, Calif.).

Oocytes were continuously superfused in frog Ringer's solution (10 mM HEPES, pH 7.2, 115 mM NaCl, 1.8 mM $CaCl_2$ and 2.5 mM KCl). No responses were observed by the application of drugs to uninjected oocytes. For the inhibition curves (see FIGS. 4B, 5A and 5B), antagonists were coapplied with 10 μM acetylcholine. In the case of α-bungarotoxin and κ-bungarotoxin (see FIGS. 6A and 6B), oocytes were preincubated with these drugs for 30 minutes.

The mean and standard error of the mean of peak current responses of at least four oocytes per experiment are represented in the Figures. All curve fits were done using Sigma Plot software (Jandel Scientific) with the following equations:

(i) Response (for concentration-response curves)=[(max-min)/(1+($EC_{50}$/concentration)$^n$)]+min, and (ii) Response (for concentration-inhibition curves)=[(max-min)/(1+(concentration/$IC_{50}$)$^n$)]+min.

Atropine sulfate, (−)-nicotine ditartrate, (+)-muscarine chloride, strychnine hydrochloride and oxotremorine-M were obtained from RBI (Natick, Mass.), kappa-Bungarotoxin was donated by Dr. V. Chiappinelli (St. Louis University Medical Center, St. Louis, Mo.). All other drugs were obtained from Sigma Chemical Co. (St. Louis, Mo.). Drugs were dissolved in frog Ringer's solution. Bovine serum albumin (100 mg/ml) was added to the toxin solutions.

EXAMPLE V

In situ Hybridization

Experiments were carried out using mid-sagittal sections of rat E16 embryos (Hybrid-ready tissue, Novagen, Madison, Wis.) and 20 μm thick coronal sections of adult rat brains, according to the protocol described by Simmons, et al. in *J. Histotechnol.*, 12, 169–181, 1989. Either $^{35}S$- or $^{32}P$-labeled RNA probes were derived from the alpha9 cDNA (e.g., nucleotides 283 to 806, FIG. 1; i.e., nucleotides 455 to 979 of SEQ ID NO:1). Hybridization was carried out at 65° C. and final washes were carried out at 72° C. in 0.1×SSC (1×SSC is 180 mM NaCl and 17 mM sodium citrate, pH 7.0). Slides were dipped in Kodak NTB-2 emulsion, developed in Kodak D19 after 3 weeks exposure at 4° C. and subsequently Nissl stained.

EXAMPLE VI

Amplification Reactions

Tissues were obtained from adult Sprague Dawley rats. The animals were decapitated and the tissues were quickly dissected and immersed in liquid nitrogen. Total RNA was isolated according to Chomczynski and Sacchi (see *Analytical Biochem.*, 162, 156–159, 1987), using the TRIzol reagent (Gibco BRL, Gaithersburg, Md.). First strand cDNA was synthesized from 2 μg of total RNA with the Superscript Preamplification System (Gibco BRL). An aliquot containing 50 ng of cDNA was used as template in amplification reactions. The following specific primers for alpha9 were employed: sense primer, nucleotides 778 to 802; antisense primer, nucleotide 1353 to 1327 (FIG. 1; nucleotides 951 to 975 and nucleotides 1526 to 1500, respectively, of SEQ ID NO:1). The predicted fragment spans one intron-exon boundary. A 573 base pair band is expected in the case of amplification from cDNA, whereas a fragment of ~1450 bp would result from the amplification of contaminant genomic DNA. Reactions were done in the following reaction mixture: 5 U of Tag DNA polymerase, 5 U of Tag enhancer (Stratagene, La Jolla, Calif.), 5 μM of each primer, 50 μM each of dATP, dGTP, dCTP and dTTP, 20 mM Tris-HCl, pH 8.5, 10 mM $(H_4N)_2SO_4$, 2 mM $MgSO_4$, 0.1% Triton X-100 and 0.1 mg/ml bovine serum albumin. Cycle parameters were: 2 min. at 95° C. followed by 34 cycles each of 1 min. at 55° C., 1 min. at 72° C., 30 sec. at 95° C. and a final cycle of 1 min. at 55° C., 5 min. at 72° C.

EXAMPLE VII

Detection of alpha9 Transcripts in Rat Cochlea

To determine if the alpha9 gene is expressed in rat cochlea, amplification reactions were performed on cDNA reverse transcribed from cochlear total RNA. As described in Example V, two primers specific for the alpha9 sequence were employed in order to amplify a fragment that spans an intron-exon boundary and additionally to avoid possible amplification from genomic DNA. Since alpha9 is present in the rat olfactory epithelium, cDNA obtained from this tissue was used as a positive control. Sciatic nerve cDNA was included to rule out the possibility that, with the parameters used for the amplification reactions, very small amounts of transcripts would be detected in any tissue studied. Whereas no DNA was amplified from the sciatic nerve using specific primers for alpha9 (FIG. 8), both alpha3 and alpha4 subunits could be detected in this tissue with the respective specific primers.

A fragment of the expected size (573 bp) for amplification from alpha9 cDNA was obtained in the rat cochlea. Restriction endonuclease analysis of the fragment with AccI, HinfI and NcoI, further confirmed that this fragment had been derived from alpha9 transcripts.

Although the invention has been described with reference to the specific embodiments, those skilled in the art will readily appreciate that the specific experiments taught hereinabove are only illustrative of the invention. It should be understood that various modifications and variations can be made without departing from the spirit and scope of the invention.

SUMMARY OF SEQUENCES

Sequence ID No. 1 is the nucleic acid sequence (and the deduced amino acid sequence) of a cDNA encoding alpha9 nicotinic acetylcholine receptor subunit of the present invention.

Sequence ID No. 2 is the deduced amino acid sequence of the alpha9 nicotinic acetylcholine receptor subunit of the present invention.

Sequence ID No. 3 is the amino acid sequence of the rat alpha1 nicotinic acetylcholine receptor subunit.

Sequence ID No. 4 is the amino acid sequence of the rat alpha2 nicotinic acetylcholine receptor subunit.

Sequence ID No. 5 is the amino acid sequence of the rat alpha3 nicotinic acetylcholine receptor subunit.

Sequence ID No. 6 is the amino acid sequence of the rat alpha4 nicotinic acetylcholine receptor subunit.

Sequence ID No. 7 is the amino acid sequence of the rat alpha7 nicotinic acetylcholine receptor subunit.

Sequence ID No. 8 is the amino acid sequence of the chick alpha8 nicotinic acetylcholine receptor subunit.

What is claimed is:

1. Isolated nucleic acid encoding an alpha9 nicotinic acetylcholine receptor (nAChR) subunit.

2. Isolated nucleic acid according to claim 1, wherein said nucleic acid is DNA.

3. DNA according to claim 2, wherein said DNA is a cDNA.

4. DNA according to claim 2, wherein said DNA encodes the amino acid sequence set forth in SEQ ID NO:2.

5. DNA according to claim 2, wherein said DNA hybridizes under high stringency conditions to the nucleotide sequence set forth in SEQ ID NO:1.

6. DNA according to claim 2, wherein the nucleotide sequence of said DNA is at least 90% identical to the nucleotide sequence set forth in SEQ ID NO:1.

7. A vector comprising DNA according to claim 2.

8. A host cell containing a vector according to claim 7.

9. A host cell according to claim 8, wherein said cell expresses functional nACh receptor comprising at least one alpha9 nAChR subunit.

10. A host cell according to claim 9, wherein said receptor is homomeric.

11. A host cell according to claim 9, wherein said receptor is heteromeric.

12. Isolated mRNA complementary to DNA according to claim 2.

13. A nucleic acid probe comprising at least 14 contiguous nucleotides according to the nucleotide sequence set forth in SEQ ID NO:1.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1938 base pairs
( B ) TYPE: nucleic acid
( C ) STRANDEDNESS: single
( D ) TOPOLOGY: unknown ( i i ) MOLECULE TYPE: cDNA ( i i i ) HYPOTHETICAL: NO ( i v ) ANTI-SENSE: NO ( v i i ) IMMEDIATE SOURCE:
( B ) CLONE: ALPHA 9

( i x ) FEATURE:
( A ) NAME/KEY: CDS
( B ) LOCATION: 89..1525

( x i ) SEQUENCE DESCRIPTION: SEQ ID NO:1:

```
CGGTGGCAGT GAGGGTGTTT TGAGCCCTTC ACAGACAGAA GTGGGAGTCC TCGCTGTCTG   60

CCTGACACAT TCTACATGTT GGGAAAAG ATG AAC CGG CCC CAT TCC TGC CTC     112
                               Met Asn Arg Pro His Ser Cys Leu
                                1               5

TCC TTT TGC TGG ATG TAT TTT GCT GCT TCT GGA ATC AGA GCC GTA GAG    160
Ser Phe Cys Trp Met Tyr Phe Ala Ala Ser Gly Ile Arg Ala Val Glu
    10                  15                  20

ACA GCA AAT GGG AAA TAT GCT CAG AAA TTG TTC AGC GAT CTT TTT GAA    208
Thr Ala Asn Gly Lys Tyr Ala Gln Lys Leu Phe Ser Asp Leu Phe Glu
25                  30                  35                  40

GAC TAC TCC AGT GCT CTG CGT CCA GTC GAG GAT ACG GAC GCG GTG CTG    256
Asp Tyr Ser Ser Ala Leu Arg Pro Val Glu Asp Thr Asp Ala Val Leu
                45                  50                  55

AAT GTT ACA CTG CAG GTC ACG CTC TCC CAG ATA AAG GAC ATG GAC GAG    304
Asn Val Thr Leu Gln Val Thr Leu Ser Gln Ile Lys Asp Met Asp Glu
            60                  65                  70

AGA AAC CAG ATT CTG ACA GCC TAT CTA TGG ATC CGC CAA ACC TGG CAC    352
Arg Asn Gln Ile Leu Thr Ala Tyr Leu Trp Ile Arg Gln Thr Trp His
        75                  80                  85

GAT GCG TAC CTC ACG TGG GAT CGA GAC CAG TAT GAT AGG CTG GAC TCC    400
Asp Ala Tyr Leu Thr Trp Asp Arg Asp Gln Tyr Asp Arg Leu Asp Ser
    90                  95                  100

ATC AGG ATT CCC AGC GAT CTG GTG TGG AGG CCG GAC ATT GTC CTA TAC    448
Ile Arg Ile Pro Ser Asp Leu Val Trp Arg Pro Asp Ile Val Leu Tyr
105                 110                 115                 120

AAC AAG GCT GAC GAT GAG TCT TCA GAG CCT GTG AAC ACC AAT GTG GTG    496
Asn Lys Ala Asp Asp Glu Ser Ser Glu Pro Val Asn Thr Asn Val Val
                125                 130                 135

CTG CGA TAT GAT GGG CTC ATC ACC TGG GAC TCA CCG GCC ATC ACC AAA    544
Leu Arg Tyr Asp Gly Leu Ile Thr Trp Asp Ser Pro Ala Ile Thr Lys
            140                 145                 150

AGC TCC TGT GTG GTG GAT GTC ACC TAC TTC CCT TTT GAC AGC CAG CAG    592
Ser Ser Cys Val Val Asp Val Thr Tyr Phe Pro Phe Asp Ser Gln Gln
        155                 160                 165

TGC AAC CTG ACC TTT GGC TCC TGG ACC TAC AAT GGA AAC CAG GTG GAC    640
Cys Asn Leu Thr Phe Gly Ser Trp Thr Tyr Asn Gly Asn Gln Val Asp
    170                 175                 180
```

-continued

```
ATA TTC AAT GCC CTG GAC AGC GGT GAC CTC TCT GAC TTC ATT GAA GAT    688
Ile Phe Asn Ala Leu Asp Ser Gly Asp Leu Ser Asp Phe Ile Glu Asp
185                 190                 195                 200

GTG GAA TGG GAG GTC CAT GGC ATG CCT GCT GTA AAG AAC GTC ATC TCC    736
Val Glu Trp Glu Val His Gly Met Pro Ala Val Lys Asn Val Ile Ser
                205                 210                 215

TAT GGC TGC TGC TCC GAG CCT TAC CCA GAT GTC ACC TTC ACT CTC CTT    784
Tyr Gly Cys Cys Ser Glu Pro Tyr Pro Asp Val Thr Phe Thr Leu Leu
            220                 225                 230

CTG AAG AGG AGG TCC TCC TTC TAC ATC GTC AAC CTC CTC ATC CCT TGC    832
Leu Lys Arg Arg Ser Ser Phe Tyr Ile Val Asn Leu Leu Ile Pro Cys
        235                 240                 245

GTC CTC ATA TCG TTC CTC GCT CCG TTG AGT TTC TAT CTC CCA GCA GCC    880
Val Leu Ile Ser Phe Leu Ala Pro Leu Ser Phe Tyr Leu Pro Ala Ala
    250                 255                 260

TCT GGG GAG AAG GTC TCT CTG GGA GTG ACC ATC CTA TTG GCC ATG ACT    928
Ser Gly Glu Lys Val Ser Leu Gly Val Thr Ile Leu Leu Ala Met Thr
265                 270                 275                 280

GTG TTT CAG CTA ATG GTG GCA GAG ATC ATG CCA GCC TCA GAA AAT GTC    976
Val Phe Gln Leu Met Val Ala Glu Ile Met Pro Ala Ser Glu Asn Val
                285                 290                 295

CCT CTG ATA GGA AAA TAC TAC ATA GCT ACC ATG GCC TTG ATC ACT GCC   1024
Pro Leu Ile Gly Lys Tyr Tyr Ile Ala Thr Met Ala Leu Ile Thr Ala
            300                 305                 310

TCC ACA GCC CTT ACC ATC ATG GTG ATG AAT ATT CAC TTC TGT GGA GCT   1072
Ser Thr Ala Leu Thr Ile Met Val Met Asn Ile His Phe Cys Gly Ala
        315                 320                 325

GAG GCA CGG CCA GTG CCA CAC TGG GCC AAG GTG GTC ATC CTG AAG TAC   1120
Glu Ala Arg Pro Val Pro His Trp Ala Lys Val Val Ile Leu Lys Tyr
    330                 335                 340

ATG TCC AGG ATC TTG TTT GTC TAC GAT GTG GGT GAG AGC TGC CTT AGT   1168
Met Ser Arg Ile Leu Phe Val Tyr Asp Val Gly Glu Ser Cys Leu Ser
345                 350                 355                 360

CCC CGC CAC AGC CAG GAG CCA GAA CAA GTC ACG AAG GTT TAT AGC AAA   1216
Pro Arg His Ser Gln Glu Pro Glu Gln Val Thr Lys Val Tyr Ser Lys
                365                 370                 375

CTC CCA GAA TCC AAC CTG AAA ACG TCC AGA AAC AAA GAC CTT TCC AGA   1264
Leu Pro Glu Ser Asn Leu Lys Thr Ser Arg Asn Lys Asp Leu Ser Arg
            380                 385                 390

AAG AAG GAA GTA AGA AAA CTC TTA AAG AAT GAC CTG GGG TAC CAG GGT   1312
Lys Lys Glu Val Arg Lys Leu Leu Lys Asn Asp Leu Gly Tyr Gln Gly
        395                 400                 405

GGG ATC CCC CAG AAT ACT GAC AGT TAT TGT GCA CGC TAT GAA GCA CTG   1360
Gly Ile Pro Gln Asn Thr Asp Ser Tyr Cys Ala Arg Tyr Glu Ala Leu
    410                 415                 420

GCG AAA AAT ATC GAA TAC ATT GCC AAG TGC CTC AAG GAC CAC AAG GCC   1408
Ala Lys Asn Ile Glu Tyr Ile Ala Lys Cys Leu Lys Asp His Lys Ala
425                 430                 435                 440

ACC AAC TCC AAG GGC AGC GAG TGG AAG AAG GTC GCC AAA GTC ATA GAC   1456
Thr Asn Ser Lys Gly Ser Glu Trp Lys Lys Val Ala Lys Val Ile Asp
                445                 450                 455

CGT TTC TTC ATG TGG ATT TTC TTT GCT ATG GTG TTT GTC ATG ACC GTC   1504
Arg Phe Phe Met Trp Ile Phe Phe Ala Met Val Phe Val Met Thr Val
            460                 465                 470

TTG ATC ATA GCA AGA GCA GAT TAGCAGGAAA GAGGAGTGGG CTGGTAGGCA      1555
Leu Ile Ile Ala Arg Ala Asp
        475

TTTAGAGATT TGGGGAAAAC CCAATAAAAT CACCTGAGAT CTGCCCCAGC GTGTGAGTTC 1615

AGCTGCTGTT CATACATAAT TTAGGGGATA GGTTGCGTAT GCTTTTATTC CTAACTTCAA 1675
```

-continued

TCAATATCCT AGTTACATGT CAGGTTAAAT CAAGCAGGAG ATGCAAGGTT TCAAGGGTAA 1735

AGGGCTGGAG GAAGAGAGTT AGAAAGGACC CTTTCACAGG CTCCCATGAA GGGGAGTGGT 1795

GGCCTTCAGT TTATGTAATT ATCTCTTTAT TATTGTAGAC AACAAAGCAC AGTGTATTCC 1855

TGCTTAAGAT TTAAAGCAAG AAAAGACAAA ACAAATTCAT TCTCTTAGTC CTTAATAAAA 1915

CTTTTTTTTT TAAACAAAAA AAA 1938

(2) INFORMATION FOR SEQ ID NO:2:

(i) SEQUENCE CHARACTERISTICS:
(A) LENGTH: 479 amino acids
(B) TYPE: amino acid
(D) TOPOLOGY: linear (ii) MOLECULE TYPE: protein (xi) SEQUENCE DESCRIPTION: SEQ ID NO:2:

Met Asn Arg Pro His Ser Cys Leu Ser Phe Cys Trp Met Tyr Phe Ala
1 5 10 15

Ala Ser Gly Ile Arg Ala Val Glu Thr Ala Asn Gly Lys Tyr Ala Gln
20 25 30

Lys Leu Phe Ser Asp Leu Phe Glu Asp Tyr Ser Ser Ala Leu Arg Pro
35 40 45

Val Glu Asp Thr Asp Ala Val Leu Asn Val Thr Leu Gln Val Thr Leu
50 55 60

Ser Gln Ile Lys Asp Met Asp Glu Arg Asn Gln Ile Leu Thr Ala Tyr
65 70 75 80

Leu Trp Ile Arg Gln Thr Trp His Asp Ala Tyr Leu Thr Trp Asp Arg
85 90 95

Asp Gln Tyr Asp Arg Leu Asp Ser Ile Arg Ile Pro Ser Asp Leu Val
100 105 110

Trp Arg Pro Asp Ile Val Leu Tyr Asn Lys Ala Asp Asp Glu Ser Ser
115 120 125

Glu Pro Val Asn Thr Asn Val Val Leu Arg Tyr Asp Gly Leu Ile Thr
130 135 140

Trp Asp Ser Pro Ala Ile Thr Lys Ser Ser Cys Val Val Asp Val Thr
145 150 155 160

Tyr Phe Pro Phe Asp Ser Gln Gln Cys Asn Leu Thr Phe Gly Ser Trp
165 170 175

Thr Tyr Asn Gly Asn Gln Val Asp Ile Phe Asn Ala Leu Asp Ser Gly
180 185 190

Asp Leu Ser Asp Phe Ile Glu Asp Val Glu Trp Glu Val His Gly Met
195 200 205

Pro Ala Val Lys Asn Val Ile Ser Tyr Gly Cys Cys Ser Glu Pro Tyr
210 215 220

Pro Asp Val Thr Phe Thr Leu Leu Leu Lys Arg Arg Ser Ser Phe Tyr
225 230 235 240

Ile Val Asn Leu Leu Ile Pro Cys Val Leu Ile Ser Phe Leu Ala Pro
245 250 255

Leu Ser Phe Tyr Leu Pro Ala Ala Ser Gly Glu Lys Val Ser Leu Gly
260 265 270

Val Thr Ile Leu Leu Ala Met Thr Val Phe Gln Leu Met Val Ala Glu
275 280 285

Ile Met Pro Ala Ser Glu Asn Val Pro Leu Ile Gly Lys Tyr Tyr Ile
290 295 300

-continued

Ala Thr Met Ala Leu Ile Thr Ala Ser Thr Ala Leu Thr Ile Met Val
305 310 315 320

Met Asn Ile His Phe Cys Gly Ala Glu Ala Arg Pro Val Pro His Trp
325 330 335

Ala Lys Val Val Ile Leu Lys Tyr Met Ser Arg Ile Leu Phe Val Tyr
340 345 350

Asp Val Gly Glu Ser Cys Leu Ser Pro Arg His Ser Gln Glu Pro Glu
355 360 365

Gln Val Thr Lys Val Tyr Ser Lys Leu Pro Glu Ser Asn Leu Lys Thr
370 375 380

Ser Arg Asn Lys Asp Leu Ser Arg Lys Lys Glu Val Arg Lys Leu Leu
385 390 395 400

Lys Asn Asp Leu Gly Tyr Gln Gly Gly Ile Pro Gln Asn Thr Asp Ser
405 410 415

Tyr Cys Ala Arg Tyr Glu Ala Leu Ala Lys Asn Ile Glu Tyr Ile Ala
420 425 430

Lys Cys Leu Lys Asp His Lys Ala Thr Asn Ser Lys Gly Ser Glu Trp
435 440 445

Lys Lys Val Ala Lys Val Ile Asp Arg Phe Phe Met Trp Ile Phe Phe
450 455 460

Ala Met Val Phe Val Met Thr Val Leu Ile Ile Ala Arg Ala Asp
465 470 475

( 2 ) INFORMATION FOR SEQ ID NO:3:

( i ) SEQUENCE CHARACTERISTICS:
( A ) LENGTH: 457 amino acids
( B ) TYPE: amino acid
( D ) TOPOLOGY: linear ( i i ) MOLECULE TYPE: protein ( x i ) SEQUENCE DESCRIPTION: SEQ ID NO:3:

Met Glu Leu Ser Thr Val Leu Leu Leu Leu Gly Leu Ser Ser Ala Gly
1 5 10 15

Leu Val Leu Gly Ser Glu His Glu Thr Arg Leu Val Ala Lys Leu Phe
20 25 30

Glu Asp Tyr Ser Ser Val Val Arg Pro Val Glu Asp His Arg Glu Ile
35 40 45

Val Gln Val Thr Val Gly Leu Gln Leu Ile Gln Leu Ile Asn Val Asp
50 55 60

Glu Val Asn Gln Ile Val Thr Thr Asn Val Arg Leu Lys Gln Gln Trp
65 70 75 80

Val Asp Tyr Asn Leu Lys Trp Asn Pro Asp Asp Tyr Gly Gly Val Lys
85 90 95

Lys Ile His Ile Pro Ser Glu Lys Ile Trp Arg Pro Asp Val Val Leu
100 105 110

Tyr Asn Asn Ala Asp Gly Asp Phe Ala Ile Val Lys Phe Thr Lys Val
115 120 125

Leu Leu Asp Tyr Thr Gly His Ile Thr Trp Thr Pro Pro Ala Ile Phe
130 135 140

Lys Ser Tyr Cys Glu Ile Ile Val Thr His Phe Pro Phe Asp Glu Gln
145 150 155 160

Asn Cys Ser Met Lys Leu Gly Thr Trp Thr Tyr Asp Gly Ser Val Val
165 170 175

Ala Ile Asn Pro Glu Ser Asp Gln Pro Asp Leu Ser Asn Phe Met Glu
180 185 190

-continued

Ser Gly Glu Trp Val Ile Lys Glu Ala Arg Gly Trp Lys His Trp Val
195 200 205

Phe Tyr Ser Cys Cys Pro Thr Thr Pro Tyr Leu Asp Ile Thr Tyr His
210 215 220

Phe Val Met Gln Arg Leu Pro Leu Tyr Phe Ile Val Asn Val Ile Ile
225 230 235 240

Pro Cys Leu Leu Phe Ser Phe Leu Thr Ser Leu Val Phe Tyr Leu Pro
245 250 255

Thr Asp Ser Gly Glu Lys Met Thr Leu Ser Ile Ser Val Leu Leu Ser
260 265 270

Leu Thr Val Phe Leu Leu Val Ile Val Glu Leu Ile Pro Ser Thr Ser
275 280 285

Ser Ala Val Pro Leu Ile Gly Lys Tyr Met Leu Phe Thr Met Val Phe
290 295 300

Val Ile Ala Ser Ile Ile Ile Thr Val Ile Val Ile Asn Thr His His
305 310 315 320

Arg Ser Pro Ser Thr His Ile Met Pro Glu Trp Val Arg Lys Val Phe
325 330 335

Ile Asp Thr Ile Pro Asn Ile Met Phe Phe Ser Thr Met Lys Arg Pro
340 345 350

Ser Arg Asp Lys Gln Glu Lys Arg Ile Phe Thr Glu Asp Ile Asp Ile
355 360 365

Ser Asp Ile Ser Gly Lys Pro Gly Pro Pro Pro Met Gly Phe His Ser
370 375 380

Pro Leu Ile Lys His Pro Glu Val Lys Ser Ala Ile Glu Gly Val Lys
385 390 395 400

Tyr Ile Ala Glu Thr Met Lys Ser Asp Gln Glu Ser Asn Asn Ala Ala
405 410 415

Glu Glu Trp Lys Tyr Val Ala Met Val Met Asp His Ile Leu Leu Gly
420 425 430

Val Phe Met Leu Val Cys Leu Ile Gly Thr Leu Ala Val Phe Ala Gly
435 440 445

Arg Leu Ile Glu Leu His Gln Gln Gly
450 455

( 2 ) INFORMATION FOR SEQ ID NO:4:

( i ) SEQUENCE CHARACTERISTICS:
( A ) LENGTH: 510 amino acids
( B ) TYPE: amino acid
( D ) TOPOLOGY: linear ( i i ) MOLECULE TYPE: protein ( x i ) SEQUENCE DESCRIPTION: SEQ ID NO:4:

Met Thr Leu Ser His Ser Ala Leu Gln Phe Trp Thr His Leu Tyr Leu
1 5 10 15

Trp Cys Leu Leu Leu Val Pro Ala Val Leu Thr Gln Gln Gly Ser His
20 25 30

Thr His Ala Glu Asp Arg Leu Phe Lys His Leu Phe Gly Gly Tyr Asn
35 40 45

Arg Trp Ala Arg Pro Val Pro Asn Thr Ser Asp Val Val Ile Val Arg
50 55 60

Phe Gly Leu Ser Ile Ala Gln Leu Ile Asp Val Asp Glu Lys Asn Gln
65 70 75 80

Met Met Thr Thr Asn Val Trp Leu Lys Gln Glu Trp Asn Asp Tyr Asn

-continued

```
                    85                      90                      95

Val Arg Trp Asp Pro Ala Glu Phe Gly Asn Val Thr Ser Leu Arg Val
            100                 105                 110

Pro Ser Glu Met Ile Trp Ile Pro Asp Ile Val Leu Tyr Asn Asn Ala
        115                 120                 125

Asp Gly Glu Phe Ala Val Thr His Met Thr Lys Ala His Leu Phe Phe
    130                 135                 140

Thr Gly Thr Val His Trp Val Pro Pro Ala Ile Tyr Lys Ser Ser Cys
145                 150                 155                     160

Ser Ile Asp Val Thr Phe Phe Pro Phe Asp Gln Gln Asn Cys Lys Met
                165                 170                 175

Lys Phe Gly Ser Trp Thr Tyr Asp Lys Ala Lys Ile Asp Leu Glu Gln
            180                 185                 190

Met Glu Arg Thr Val Asp Leu Lys Asp Tyr Trp Glu Ser Gly Glu Trp
        195                 200                 205

Ala Ile Ile Asn Ala Thr Gly Thr Tyr Asn Ser Lys Lys Tyr Asp Cys
    210                 215                 220

Cys Ala Glu Ile Tyr Pro Asp Val Thr Tyr Tyr Phe Val Ile Arg Arg
225                 230                 235                     240

Leu Pro Leu Phe Tyr Thr Ile Asn Leu Ile Ile Pro Cys Leu Leu Ile
                245                 250                 255

Ser Cys Leu Thr Val Leu Val Phe Tyr Leu Pro Ser Glu Cys Gly Glu
            260                 265                 270

Lys Ile Thr Leu Cys Ile Ser Val Leu Leu Ser Leu Thr Val Phe Leu
        275                 280                 285

Leu Leu Ile Thr Glu Ile Ile Pro Ser Thr Ser Leu Val Ile Pro Leu
    290                 295                 300

Ile Gly Glu Tyr Leu Leu Phe Thr Met Ile Phe Val Thr Leu Ser Ile
305                 310                 315                     320

Val Ile Thr Val Phe Val Leu Asn Val His His Arg Ser Pro Ser Thr
                325                 330                 335

His Asn Met Pro Asn Trp Val Arg Val Ala Leu Leu Gly Arg Val Pro
            340                 345                 350

Arg Trp Leu Met Met Asn Arg Pro Leu Pro Pro Met Glu Leu His Gly
        355                 360                 365

Ser Pro Asp Leu Lys Leu Ser Pro Ser Tyr His Trp Leu Glu Thr Asn
    370                 375                 380

Met Asp Ala Gly Glu Arg Glu Glu Thr Glu Glu Glu Glu Glu Glu Asp
385                 390                 395                     400

Glu Asn Ile Cys Val Cys Ala Gly Leu Pro Asp Ser Ser Met Gly Val
                405                 410                 415

Leu Tyr Gly His Gly Gly Leu His Leu Arg Ala Met Glu Pro Glu Thr
            420                 425                 430

Lys Thr Pro Ser Gln Ala Ser Glu Ile Leu Leu Ser Pro Gln Ile Gln
        435                 440                 445

Lys Ala Leu Glu Gly Val His Tyr Ile Ala Asp Arg Leu Arg Ser Glu
    450                 455                 460

Asp Ala Asp Ser Ser Val Lys Glu Asp Trp Lys Tyr Val Ala Met Val
465                 470                 475                     480

Val Asp Arg Ile Phe Leu Trp Leu Phe Ile Ile Val Cys Phe Leu Gly
                485                 490                 495

Thr Ile Gly Leu Phe Leu Pro Pro Phe Leu Ala Gly Met Ile
            500                 505                 510
```

-continued ( 2 ) INFORMATION FOR SEQ ID NO:5:

( i ) SEQUENCE CHARACTERISTICS:
( A ) LENGTH: 497 amino acids
( B ) TYPE: amino acid
( D ) TOPOLOGY: linear ( i i ) MOLECULE TYPE: protein ( x i ) SEQUENCE DESCRIPTION: SEQ ID NO:5:

| | | | | | | | | | | | | | | | |
|---|---|---|---|---|---|---|---|---|---|---|---|---|---|---|---|
| Met | Gly | Val | Val | Leu | Leu | Pro | Pro | Pro | Leu | Ser | Met | Leu | Met | Leu | Val |
| 1 | | | | 5 | | | | | 10 | | | | | 15 | |
| Leu | Met | Leu | Leu | Pro | Ala | Ala | Ser | Glu | Ala | Glu | His | Arg | Leu | Phe | Gln |
| | | | 20 | | | | | 25 | | | | | 30 | | |
| Tyr | Leu | Phe | Glu | Asp | Tyr | Asn | Glu | Ile | Ile | Arg | Pro | Val | Ala | Asn | Val |
| | | 35 | | | | | 40 | | | | | 45 | | | |
| Ser | His | Pro | Val | Ile | Ile | Gln | Phe | Glu | Val | Ser | Met | Ser | Gln | Leu | Val |
| | 50 | | | | | 55 | | | | | 60 | | | | |
| Lys | Val | Asp | Glu | Val | Asn | Gln | Ile | Met | Glu | Thr | Asn | Leu | Trp | Leu | Lys |
| 65 | | | | | 70 | | | | | 75 | | | | | 80 |
| Gln | Ile | Trp | Asn | Asp | Tyr | Lys | Leu | Lys | Trp | Lys | Pro | Ser | Asp | Tyr | Gln |
| | | | | 85 | | | | | 90 | | | | | 95 | |
| Gly | Val | Glu | Phe | Met | Arg | Val | Pro | Ala | Glu | Lys | Ile | Trp | Lys | Pro | Asp |
| | | | 100 | | | | | 105 | | | | | 110 | | |
| Ile | Val | Leu | Tyr | Asn | Asn | Ala | Asp | Gly | Asp | Phe | Gln | Val | Asp | Asp | Lys |
| | | 115 | | | | | 120 | | | | | 125 | | | |
| Thr | Lys | Ala | Leu | Leu | Lys | Tyr | Thr | Gly | Glu | Val | Thr | Trp | Ile | Pro | Pro |
| | 130 | | | | | 135 | | | | | 140 | | | | |
| Ala | Ile | Phe | Lys | Ser | Ser | Cys | Lys | Ile | Asp | Val | Thr | Tyr | Phe | Pro | Phe |
| 145 | | | | | 150 | | | | | 155 | | | | | 160 |
| Asp | Tyr | Gln | Asn | Cys | Thr | Met | Lys | Phe | Gly | Ser | Trp | Ser | Tyr | Asp | Lys |
| | | | | 165 | | | | | 170 | | | | | 175 | |
| Ala | Lys | Ile | Asp | Leu | Val | Leu | Ile | Gly | Ser | Ser | Met | Asn | Leu | Lys | Asp |
| | | | 180 | | | | | 185 | | | | | 190 | | |
| Tyr | Trp | Glu | Ser | Gly | Glu | Trp | Ala | Ile | Ile | Lys | Ala | Pro | Gly | Tyr | Lys |
| | | 195 | | | | | 200 | | | | | 205 | | | |
| His | Glu | Ile | Lys | Tyr | Asn | Cys | Cys | Glu | Glu | Ile | Tyr | Gln | Asp | Ile | Thr |
| | 210 | | | | | 215 | | | | | 220 | | | | |
| Tyr | Ser | Leu | Tyr | Ile | Arg | Arg | Leu | Pro | Leu | Phe | Tyr | Thr | Ile | Asn | Leu |
| 225 | | | | | 230 | | | | | 235 | | | | | 240 |
| Ile | Ile | Pro | Cys | Leu | Leu | Ile | Ser | Phe | Leu | Thr | Val | Leu | Val | Phe | Tyr |
| | | | | 245 | | | | | 250 | | | | | 255 | |
| Leu | Pro | Ser | Asp | Cys | Gly | Glu | Lys | Val | Thr | Leu | Cys | Ile | Ser | Val | Leu |
| | | | 260 | | | | | 265 | | | | | 270 | | |
| Leu | Ser | Leu | Thr | Val | Phe | Leu | Leu | Val | Ile | Thr | Glu | Thr | Ile | Pro | Ser |
| | | 275 | | | | | 280 | | | | | 285 | | | |
| Thr | Ser | Leu | Val | Ile | Pro | Leu | Ile | Gly | Glu | Tyr | Leu | Leu | Phe | Thr | Met |
| | 290 | | | | | 295 | | | | | 300 | | | | |
| Ile | Phe | Val | Thr | Leu | Ser | Ile | Val | Ile | Thr | Val | Phe | Val | Leu | Asn | Val |
| 305 | | | | | 310 | | | | | 315 | | | | | 320 |
| His | Tyr | Arg | Thr | Pro | Thr | Thr | His | Thr | Met | Pro | Thr | Trp | Val | Lys | Ala |
| | | | | 325 | | | | | 330 | | | | | 335 | |
| Val | Phe | Leu | Asn | Leu | Leu | Pro | Arg | Val | Met | Phe | Met | Thr | Arg | Pro | Thr |
| | | | 340 | | | | | 345 | | | | | 350 | | |
| Ser | Gly | Glu | Gly | Asp | Thr | Pro | Lys | Thr | Arg | Thr | Phe | Tyr | Gly | Ala | Glu |
| | | 355 | | | | | 360 | | | | | 365 | | | |

-continued

Leu Ser Asn Leu Asn Cys Phe Ser Arg Ala Asp Ser Lys Ser Cys Lys
370 375 380

Glu Gly Tyr Pro Cys Gln Asp Gly Thr Cys Gly Tyr Cys His His Arg
385 390 395 400

Arg Val Lys Ile Ser Asn Phe Ser Ala Asn Leu Thr Arg Ser Ser Ser
405 410 415

Ser Glu Ser Val Asn Ala Val Leu Ser Leu Ser Ala Leu Ser Pro Glu
420 425 430

Ile Lys Glu Ala Ile Gln Ser Val Lys Tyr Ile Ala Glu Asn Met Lys
435 440 445

Ala Gln Asn Val Ala Lys Glu Ile Gln Asp Asp Trp Lys Tyr Val Ala
450 455 460

Met Val Ile Asp Arg Ile Phe Leu Trp Val Phe Ile Leu Val Cys Ile
465 470 475 480

Leu Gly Thr Ala Gly Leu Phe Leu Gln Pro Leu Met Ala Arg Asp Asp
485 490 495

Thr ( 2 ) INFORMATION FOR SEQ ID NO:6:

( i ) SEQUENCE CHARACTERISTICS:
( A ) LENGTH: 629 amino acids
( B ) TYPE: amino acid
( D ) TOPOLOGY: linear ( i i ) MOLECULE TYPE: protein ( x i ) SEQUENCE DESCRIPTION: SEQ ID NO:6:

Met Glu Ile Gly Gly Pro Gly Ala Pro Pro Pro Leu Leu Leu Leu Pro
1 5 10 15

Leu Leu Leu Leu Leu Gly Thr Gly Leu Leu Pro Ala Ser Ser His Ile
20 25 30

Glu Thr Arg Ala His Ala Glu Glu Arg Leu Leu Lys Arg Leu Phe Ser
35 40 45

Gly Tyr Asn Lys Trp Ser Arg Pro Val Gly Asn Ile Ser Asp Val Val
50 55 60

Leu Val Arg Phe Gly Leu Ser Ile Ala Gln Leu Ile Asp Val Asp Glu
65 70 75 80

Lys Asn Gln Met Met Thr Thr Asn Val Trp Val Lys Gln Glu Trp His
85 90 95

Asp Tyr Lys Leu Arg Trp Asp Pro Gly Asp Tyr Glu Asn Val Thr Ser
100 105 110

Ile Arg Ile Pro Ser Glu Leu Ile Trp Arg Pro Asp Ile Val Leu Tyr
115 120 125

Asn Asn Ala Asp Gly Asp Phe Ala Val Thr His Leu Thr Lys Ala His
130 135 140

Leu Phe Tyr Asp Gly Arg Val Gln Trp Thr Pro Pro Ala Ile Tyr Lys
145 150 155 160

Ser Ser Cys Ser Ile Asp Val Thr Phe Phe Pro Phe Asp Gln Gln Asn
165 170 175

Cys Thr Met Lys Phe Gly Ser Trp Thr Tyr Asp Lys Ala Lys Ile Asp
180 185 190

Leu Val Ser Ile His Ser Arg Val Asp Gln Leu Asp Phe Trp Glu Ser
195 200 205

Gly Glu Trp Val Ile Val Asp Ala Val Gly Thr Tyr Asn Thr Arg Lys
210 215 220

-continued

Tyr Glu Cys Cys Ala Glu Ile Tyr Pro Asp Ile Thr Tyr Ala Phe Ile
225 230 235 240

Ile Arg Arg Leu Pro Leu Phe Tyr Thr Ile Asn Leu Ile Ile Pro Cys
245 250 255

Leu Leu Ile Ser Cys Leu Thr Val Leu Val Phe Tyr Leu Pro Ser Glu
260 265 270

Cys Gly Glu Lys Val Thr Cys Ala Ser Ser Val Leu Leu Ser Leu Thr
275 280 285

Val Phe Leu Leu Leu Ile Thr Glu Ile Ile Pro Ser Thr Ser Leu Val
290 295 300

Ile Pro Leu Ile Gly Glu Tyr Leu Leu Phe Thr Met Ile Phe Val Thr
305 310 315 320

Leu Ser Ile Val Ile Thr Val Phe Val Leu Asn Val His His Arg Ser
325 330 335

Pro Arg Thr His Thr Met Pro Ala Trp Val Arg Arg Val Phe Leu Asp
340 345 350

Ile Val Pro Arg Leu Leu Phe Met Lys Arg Pro Ser Val Val Lys Asp
355 360 365

Asn Cys Arg Arg Leu Ile Glu Ser Met His Lys Met Ala Asn Ala Pro
370 375 380

Arg Phe Trp Pro Glu Pro Val Gly Glu Pro Gly Ile Leu Ser Asp Ile
385 390 395 400

Cys Asn Gln Gly Leu Ser Pro Ala Pro Thr Phe Cys Asn Pro Thr Asp
405 410 415

Thr Ala Val Glu Thr Gln Pro Thr Cys Arg Ser Pro Pro Leu Glu Val
420 425 430

Pro Asp Leu Lys Thr Ser Glu Val Glu Lys Ala Ser Pro Cys Pro Ser
435 440 445

Pro Gly Ser Cys Pro Pro Pro Lys Ser Ser Ser Gly Ala Pro Met Leu
450 455 460

Ile Lys Ala Arg Ser Leu Ser Val Gln His Val Pro Ser Ser Gln Glu
465 470 475 480

Ala Ala Glu Asp Gly Ile Arg Cys Arg Ser Arg Ser Ile Gln Tyr Cys
485 490 495

Val Ser Gln Asp Gly Ala Ala Ser Leu Ala Asp Ser Lys Pro Thr Ser
500 505 510

Ser Pro Thr Ser Leu Lys Ala Arg Pro Ser Gln Leu Pro Val Ser Asp
515 520 525

Gln Ala Ser Pro Cys Lys Cys Thr Cys Lys Glu Pro Ser Pro Val Ser
530 535 540

Pro Val Thr Val Leu Lys Ala Gly Gly Thr Lys Ala Pro Pro Gln His
545 550 555 560

Leu Pro Leu Ser Pro Ala Leu Thr Arg Ala Val Glu Gly Val Gln Tyr
565 570 575

Ile Ala Asp His Leu Lys Ala Glu Asp Thr Asp Phe Ser Val Lys Glu
580 585 590

Asp Trp Lys Tyr Val Ala Met Val Ile Asp Arg Ile Phe Leu Trp Met
595 600 605

Phe Ile Ile Val Cys Leu Leu Gly Thr Val Gly Leu Phe Leu Pro Pro
610 615 620

Trp Leu Ala Ala Cys
625

-continued ( 2 ) INFORMATION FOR SEQ ID NO:7:

( i ) SEQUENCE CHARACTERISTICS:
( A ) LENGTH: 502 amino acids
( B ) TYPE: amino acid
( D ) TOPOLOGY: linear ( i i ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
| Met | Cys | Gly | Gly | Arg | Gly | Gly | Ile | Trp | Leu | Ala | Leu | Ala | Ala | Ala | Leu |
| 1 | | | | 5 | | | | | 10 | | | | | 15 | |
| Leu | His | Val | Ser | Leu | Gln | Gly | Glu | Phe | Gln | Arg | Arg | Leu | Tyr | Lys | Glu |
| | | | 20 | | | | | 25 | | | | | 30 | | |
| Leu | Val | Lys | Asn | Tyr | Asn | Pro | Leu | Glu | Arg | Pro | Val | Ala | Asn | Asp | Ser |
| | | 35 | | | | | 40 | | | | | 45 | | | |
| Gln | Pro | Leu | Thr | Val | Tyr | Phe | Ser | Leu | Ser | Leu | Leu | Gln | Ile | Met | Asp |
| | 50 | | | | | 55 | | | | | 60 | | | | |
| Val | Asp | Glu | Lys | Asn | Gln | Val | Leu | Thr | Thr | Asn | Ile | Trp | Leu | Gln | Met |
| 65 | | | | | 70 | | | | | 75 | | | | | 80 |
| Ser | Trp | Thr | Asp | His | Tyr | Leu | Gln | Trp | Asn | Met | Ser | Glu | Tyr | Pro | Gly |
| | | | | 85 | | | | | 90 | | | | | 95 | |
| Val | Lys | Asn | Val | Arg | Phe | Pro | Asp | Gly | Gln | Ile | Trp | Lys | Pro | Asp | Ile |
| | | | 100 | | | | | 105 | | | | | 110 | | |
| Leu | Leu | Tyr | Asn | Ser | Ala | Asp | Glu | Arg | Phe | Asp | Ala | Thr | Phe | His | Thr |
| | | 115 | | | | | 120 | | | | | 125 | | | |
| Asn | Val | Leu | Val | Asn | Ala | Ser | Gly | His | Cys | Gln | Tyr | Leu | Pro | Pro | Gly |
| | 130 | | | | | 135 | | | | | 140 | | | | |
| Ile | Phe | Lys | Ser | Ser | Cys | Tyr | Ile | Asp | Val | Arg | Trp | Phe | Pro | Phe | Asp |
| 145 | | | | | 150 | | | | | 155 | | | | | 160 |
| Val | Gln | Gln | Cys | Lys | Leu | Lys | Phe | Gly | Ser | Trp | Ser | Tyr | Gly | Gly | Trp |
| | | | | 165 | | | | | 170 | | | | | 175 | |
| Ser | Leu | Asp | Leu | Gln | Met | Gln | Glu | Ala | Asp | Ile | Ser | Ser | Tyr | Ile | Pro |
| | | | 180 | | | | | 185 | | | | | 190 | | |
| Asn | Gly | Glu | Trp | Asp | Leu | Met | Gly | Ile | Pro | Gly | Lys | Arg | Asn | Glu | Lys |
| | | 195 | | | | | 200 | | | | | 205 | | | |
| Phe | Tyr | Glu | Cys | Cys | Lys | Glu | Pro | Tyr | Pro | Asp | Val | Thr | Tyr | Thr | Val |
| | 210 | | | | | 215 | | | | | 220 | | | | |
| Thr | Met | Arg | Arg | Arg | Thr | Leu | Tyr | Tyr | Gly | Leu | Asn | Leu | Leu | Ile | Pro |
| 225 | | | | | 230 | | | | | 235 | | | | | 240 |
| Cys | Val | Leu | Ile | Ser | Ala | Leu | Ala | Leu | Leu | Val | Phe | Leu | Leu | Pro | Ala |
| | | | | 245 | | | | | 250 | | | | | 255 | |
| Asp | Ser | Gly | Glu | Lys | Ile | Ser | Leu | Gly | Ile | Thr | Val | Leu | Leu | Ser | Leu |
| | | | 260 | | | | | 265 | | | | | 270 | | |
| Thr | Val | Phe | Met | Leu | Leu | Val | Ala | Glu | Ile | Met | Pro | Ala | Thr | Ser | Asp |
| | | 275 | | | | | 280 | | | | | 285 | | | |
| Ser | Val | Pro | Leu | Ile | Ala | Gln | Tyr | Phe | Ala | Ser | Thr | Met | Ile | Ile | Val |
| | 290 | | | | | 295 | | | | | 300 | | | | |
| Gly | Leu | Ser | Val | Val | Val | Thr | Val | Ile | Val | Leu | Arg | Tyr | His | His | His |
| 305 | | | | | 310 | | | | | 315 | | | | | 320 |
| Asp | Pro | Asp | Gly | Gly | Lys | Met | Pro | Lys | Trp | Thr | Arg | Ile | Ile | Leu | Leu |
| | | | | 325 | | | | | 330 | | | | | 335 | |
| Asn | Trp | Cys | Ala | Trp | Phe | Leu | Arg | Met | Lys | Arg | Pro | Gly | Glu | Asp | Lys |
| | | | 340 | | | | | 345 | | | | | 350 | | |
| Val | Arg | Pro | Ala | Cys | Gln | His | Lys | Pro | Arg | Pro | Cys | Ser | Leu | Ala | Ser |
| | | 355 | | | | | 360 | | | | | 365 | | | |

-continued

Val Glu Leu Ser Ala Gly Ala Gly Pro Pro Thr Ser Asn Gly Asn Leu
370 375 380

Leu Tyr Ile Gly Phe Arg Gly Leu Glu Gly Met His Cys Ala Pro Thr
385 390 395 400

Pro Asp Ser Gly Val Val Cys Gly Arg Leu Ala Cys Ser Pro Thr His
405 410 415

Asp Glu His Leu Met His Gly Ala His Pro Ser Asp Gly Asp Pro Asp
420 425 430

Leu Ala Lys Ile Leu Glu Glu Val Arg Tyr Ile Ala Asn Arg Phe Arg
435 440 445

Cys Gln Asp Glu Ser Glu Val Ile Cys Ser Glu Trp Lys Phe Ala Ala
450 455 460

Cys Val Val Asp Arg Leu Cys Leu Met Ala Phe Ser Val Phe Thr Ile
465 470 475 480

Ile Cys Thr Ile Gly Ile Leu Met Ser Ala Pro Asn Phe Val Glu Ala
485 490 495

Val Ser Lys Asp Phe Ala
500

( 2 ) INFORMATION FOR SEQ ID NO:8:

( i ) SEQUENCE CHARACTERISTICS:
( A ) LENGTH: 511 amino acids
( B ) TYPE: amino acid
( D ) TOPOLOGY: linear ( i i ) MOLECULE TYPE: protein ( x i ) SEQUENCE DESCRIPTION: SEQ ID NO:8:

Met Leu Thr Glu Lys Cys Leu Gly Phe Phe Tyr Ser Gly Leu Cys Leu
1 5 10 15

Trp Ala Ser Leu Phe Leu Ser Phe Phe Lys Val Ser Gln Gln Gly Glu
20 25 30

Ser Gln Arg Arg Leu Tyr Arg Asp Leu Leu Arg Asn Tyr Asn Arg Leu
35 40 45

Glu Arg Pro Val Met Asn Asp Ser Gln Pro Ile Val Val Glu Leu Gln
50 55 60

Leu Ser Leu Leu Gln Ile Ile Asp Val Asp Glu Lys Asn Gln Val Leu
65 70 75 80

Ile Thr Asn Ala Trp Leu Gln Met Tyr Trp Val Asp Ile Tyr Leu Ser
85 90 95

Trp Asp Gln Tyr Glu Tyr Pro Gly Val Gln Asn Leu Arg Phe Pro Ser
100 105 110

Asp Gln Ile Trp Val Pro Asp Ile Leu Leu Tyr Asn Ser Ala Asp Glu
115 120 125

Arg Phe Asp Ala Thr Phe His Thr Asn Val Leu Val Asn Tyr Ser Gly
130 135 140

Ser Cys Gln Tyr Ile Pro Pro Gly Ile Leu Lys Ser Thr Cys Tyr Ile
145 150 155 160

Asp Val Arg Trp Phe Pro Phe Asp Val Gln Lys Cys Asp Leu Lys Phe
165 170 175

Gly Ser Trp Thr His Ser Gly Trp Leu Ile Asp Leu Gln Met Leu Glu
180 185 190

Ala Asp Ile Ser Asn Tyr Ile Ser Asn Gly Glu Trp Asp Leu Val Gly
195 200 205

Val Pro Gly Lys Arg Asn Glu Leu Tyr Tyr Glu Cys Cys Lys Glu Pro
210 215 220

-continued

| | | | | | | | | | | | | | | | |
|---|---|---|---|---|---|---|---|---|---|---|---|---|---|---|---|
| Tyr | Pro | Asp | Val | Thr | Tyr | Thr | Ile | Thr | Met | Arg | Arg | Arg | Thr | Leu | Tyr |
| 225 | | | | | 230 | | | | | 235 | | | | | 240 |
| Tyr | Gly | Leu | Asn | Leu | Leu | Ile | Pro | Cys | Val | Leu | Ile | Ser | Gly | Leu | Ala |
| | | | | 245 | | | | | 250 | | | | | 255 | |
| Leu | Leu | Val | Phe | Leu | Leu | Pro | Ala | Asp | Ser | Gly | Glu | Lys | Ile | Ser | Leu |
| | | | 260 | | | | | 265 | | | | | 270 | | |
| Gly | Ile | Thr | Val | Leu | Leu | Ser | Leu | Thr | Val | Phe | Met | Leu | Leu | Val | Ala |
| | | 275 | | | | | 280 | | | | | 285 | | | |
| Glu | Ile | Met | Pro | Ala | Thr | Ser | Asp | Ser | Val | Pro | Leu | Ile | Ala | Gln | Tyr |
| | 290 | | | | | 295 | | | | | 300 | | | | |
| Phe | Ala | Ser | Ile | Met | Val | Ile | Val | Gly | Leu | Ser | Val | Val | Val | Thr | Val |
| 305 | | | | | 310 | | | | | 315 | | | | | 320 |
| Leu | Val | Leu | Gln | Phe | His | His | His | Asp | Pro | Gln | Ala | Gly | Lys | Met | Pro |
| | | | | 325 | | | | | 330 | | | | | 335 | |
| Arg | Trp | Val | Arg | Val | Ile | Leu | Leu | Asn | Trp | Cys | Ala | Trp | Phe | Leu | Arg |
| | | | 340 | | | | | 345 | | | | | 350 | | |
| Met | Lys | Lys | Pro | Gly | Glu | Asn | Ile | Lys | Pro | Leu | Ser | Cys | Lys | Tyr | Ser |
| | | 355 | | | | | 360 | | | | | 365 | | | |
| Tyr | Pro | Lys | His | His | Pro | Ser | Leu | Lys | Asn | Thr | Glu | Met | Asn | Val | Leu |
| | 370 | | | | | 375 | | | | | 380 | | | | |
| Pro | Gly | His | Gln | Pro | Ser | Asn | Gly | Asn | Met | Ile | Tyr | Ser | Tyr | His | Thr |
| 385 | | | | | 390 | | | | | 395 | | | | | 400 |
| Met | Glu | Asn | Pro | Cys | Cys | Pro | Gln | Asn | Asn | Asp | Leu | Gly | Ser | Lys | Ser |
| | | | | 405 | | | | | 410 | | | | | 415 | |
| Gly | Lys | Ile | Thr | Cys | Pro | Leu | Ser | Glu | Asp | Asn | Glu | His | Val | Gln | Lys |
| | | | 420 | | | | | 425 | | | | | 430 | | |
| Lys | Ala | Leu | Met | Asp | Thr | Ile | Pro | Val | Ile | Val | Lys | Ile | Leu | Glu | Glu |
| | | 435 | | | | | 440 | | | | | 445 | | | |
| Val | Gln | Phe | Ile | Ala | Met | Arg | Phe | Arg | Lys | Gln | Asp | Glu | Gly | Glu | Glu |
| | 450 | | | | | 455 | | | | | 460 | | | | |
| Ile | Cys | Ser | Glu | Trp | Lys | Phe | Ala | Ala | Ala | Val | Ile | Asp | Arg | Leu | Cys |
| 465 | | | | | 470 | | | | | 475 | | | | | 480 |
| Leu | Val | Ala | Phe | Thr | Leu | Phe | Ala | Ile | Ile | Cys | Thr | Phe | Thr | Ile | Leu |
| | | | | 485 | | | | | 490 | | | | | 495 | |
| Met | Ser | Ala | Pro | Asn | Phe | Ile | Glu | Ala | Val | Ser | Lys | Asp | Phe | Thr | |
| | | | 500 | | | | | 505 | | | | | 510 | | |